(12) United States Patent
Zhang

(10) Patent No.: US 9,018,232 B2
(45) Date of Patent: Apr. 28, 2015

(54) SUBSTITUTED N-ARYL PYRIDINONES

(75) Inventor: Chengzhi Zhang, San Diego, CA (US)

(73) Assignee: Auspex Pharmaceuticals, Inc., La Jolla, CA (US)

( * ) Notice: Subject to any disclaimer, the term of this patent is extended or adjusted under 35 U.S.C. 154(b) by 0 days.

(21) Appl. No.: 14/003,106

(22) PCT Filed: Mar. 6, 2012

(86) PCT No.: PCT/US2012/027872
§ 371 (c)(1),
(2), (4) Date: Sep. 4, 2013

(87) PCT Pub. No.: WO2012/122165
PCT Pub. Date: Sep. 13, 2012

(65) Prior Publication Data
US 2013/0345264 A1  Dec. 26, 2013

Related U.S. Application Data

(60) Provisional application No. 61/450,489, filed on Mar. 8, 2011.

(51) Int. Cl.
*A61K 31/445* (2006.01)
*A61K 31/4418* (2006.01)
*C07D 213/64* (2006.01)
*A61K 31/4412* (2006.01)

(52) U.S. Cl.
CPC ......... *A61K 31/4418* (2013.01); *A61K 31/4412* (2013.01); *C07D 213/64* (2013.01)

(58) Field of Classification Search
CPC ................ A61K 31/4412; A61K 31/4418
USPC ............................................. 514/327
See application file for complete search history.

(56) References Cited

U.S. PATENT DOCUMENTS

| | | | |
|---|---|---|---|
| 5,310,562 | A | 5/1994 | Margolin |
| 5,962,478 | A | 10/1999 | Margolin |
| 6,221,335 | B1 | 4/2001 | Foster |
| 6,294,350 | B1 | 9/2001 | Peterson |
| 6,440,710 | B1 | 8/2002 | Keinan et al. |
| 6,603,008 | B1 | 8/2003 | Ando et al. |
| 7,407,973 | B2 | 8/2008 | Ozes et al. |
| 7,517,990 | B2 | 4/2009 | Ito et al. |
| 2002/0013372 | A1 | 1/2002 | Ekins |
| 2005/0158240 | A1 | 7/2005 | Nagasaki |
| 2006/0270612 | A1 | 11/2006 | Blatt et al. |
| 2007/0197695 | A1 | 8/2007 | Potyen et al. |
| 2008/0033011 | A1 | 2/2008 | Tung |
| 2008/0103122 | A1 | 5/2008 | Veltri |
| 2008/0319026 | A1 | 12/2008 | Gant et al. |
| 2009/0131485 | A1 | 5/2009 | Liu et al. |
| 2010/0190731 | A1 | 7/2010 | Olgin et al. |

FOREIGN PATENT DOCUMENTS

| | | |
|---|---|---|
| EP | 0458861 B1 | 3/1996 |
| EP | 1138329 A2 | 4/2001 |
| JP | 2005255560 | 9/2005 |
| WO | 9526325 A2 | 10/1995 |
| WO | 03068230 A1 | 8/2003 |
| WO | 2004019863 A2 | 3/2004 |
| WO | 2004105684 A2 | 12/2004 |
| WO | 2005013917 A2 | 2/2005 |
| WO | 2005038056 A2 | 4/2005 |
| WO | 2005040758 A2 | 5/2005 |
| WO | 2005110478 A2 | 11/2005 |
| WO | 2007038315 A2 | 4/2007 |
| WO | WO 2007064738 A1 * | 6/2007 |
| WO | 2008157786 A1 | 12/2008 |
| WO | 2009035598 A1 | 3/2009 |
| WO | 2010085805 A2 | 7/2010 |

OTHER PUBLICATIONS

Drug Report for Pirfenidone, Thomson Investigational Drug Database (Downloaded Sep. 17, 2008).
Kushner, DJ et al.; Pharmacological uses and perspectives of heavy water and deuterated compounds, Can J Phys Pharm 1999, 77, 79-88.
Bauer, LA et. al.; 0Influence of long-term infusions on lidocaine kinetics, Clin. Pharmacol. Ther. 1982, 433-7.
Borgstrom, L et al.; Comparative Pharmacokinetics of Unlabeled and Deuterium-Labeled Terbutaline: Demonstration of a Small Isotope Effect, J Pharm Sci, 1988, 77(11), 952-4.
Browne, T.R.; Chapter 2. Isotope Effect: Implications for Pharmaceutical Investigations, Pharm Lib 13, 1997.
Browne, T.R. et al.; Pharmacokinetic Equivalence of Stable-Isotope-Labeled and Unlabeled Drugs. Phenobarbital in Man, J Clin Pharmacol, 1982, 22, 309-315.
Burm, AGL et al.; Pharmacokinetics of Lidocaine and bupivacaine and stable isotope-labeled analogs: a study in healthy volunteers, Biopharmaceutics and Drug Disposition, 1988, 9, 85-95.
Elison, C et al.; Effect of Deuteration of N-CH$_(3)$ Group on Potency and Enzymatic N-Demethylation of Morphine, Science, 1961, 134(3485), 1078-9.
Farmer, PB, et al.; Synthesis, Metabolism, and Antitumor Activity of Deuterated Analogues of 1-(2-Choloroethyl)-3-cyclohexyl-1-nitrosourea, Journal of Medicinal Chemistry, 1978, vol. 21, No. 6, 514-20.
Fisher, MB, et al.; The complexities inherent in attempts to decrease drug clearance by blocking sites of CYP-mediated metabolism, Curr Opin Drug Discov Develop; 2006, 9(1), 101-9.
Foster, AB; Deuterium Isotope Effects in Studies of Drug Metabolism, Trends in Pharmacological Sciences, Dec. 1984, 524-7.
Helfenbein, J et al.; Isotopic Effect Study of Propofol Deuteration on the Metabolism, Activity, and Toxicity of the Anesthetic, J. Med. Chem. 2002, 45, 5806-5808.
Lee, H et al.; Deuterium Magic Angle Spinning Studies of Substrates Bound to Cytochrome P450, Biochemistry 1999, 38, 10808-10813.
Mamada, K et al.; Pharmacokinetic Equivalence of Deuterium-Labeled and Unlabeled Phenytoin, Drug Metabolism and Disposition, 1986, 14(4), 509-11.
Nelson, SD et al.; Primary and B-Secondary Deuterium Isotope Effects in N-Deethylation Reactions, Journal of Medicinal Chemistry, 1975, vol. 18, No. 11.

(Continued)

*Primary Examiner* — Kevin E Weddington
(74) *Attorney, Agent, or Firm* — Dennis A. Bennett

(57) ABSTRACT

Disclosed herein are methods of administering deuterated pirfenidone and kits thereof.

18 Claims, No Drawings

(56) References Cited

OTHER PUBLICATIONS

Pohl, LR et al.; Determination of toxic Pathways of Metabolism by Deuterium Substitution, Drug Metabolism Rev 1985, 1335.
Rampe, D et al.; Deuterated Analogs of verapamil and nifedipine. Synthesis and biological activity, Eur J Med Chem (1993) 28, 259-263.
Lee et al., Pirfenidone: A Novel Pharmacological Agent That Inhibits Leiomyoma Cell Proliferation and Collagen Production, J. Clin. Endocrin. Metab., 1998, 83(1), 219-23 (XP-002261363).
"Database 1Chemcats [Online], Chemical Abstract Service," Supplier: Toronto Research Chemicals Inc., XP-002495500, 2008.
CAS Registry No. 1020719-62-3, APAC Pharmaceutical Product list, APAC Pharmaceutical, LLC, published Aug. 21, 2008.
CAS Registry No. 1020719-62-3, APAC Pharmaceutical Product list, APAC Pharmaceutical, LLC, first viewed by applicant Sep. 4, 2008.
US Biological/Catalog #H9110-19W, 3-Hydroxy-5-methyl-N-phenyl-2-1H-pyridone-d5, http://www.usbio.net/displayPage.php?ProdSku=H9110-19W, first viewed by applicant Sep. 4, 2008.
Shah, Banu, FDA Core Presentation, Pirfenidone, Downloaded from http://www.fda.gov/downloads/AdvisoryCommittees/CommitteesMeetingMaterials/Drugs/Pulmonary-AllergyDrugsAdvisoryCommittee/UCM206398.pdf, Mar. 9, 2010.
Cain et al., Inhibition of tumor necrosis factor and subsequent endotoxin shock by pirfenidone, Intl. J. Immunopharm., 1998, 20, 685-695.
European Medicines Agency Committee for Medicinal Products for Human Use, European Medicines Agency CHMP Assessment Report on Esbriet (Pirfenidone), EMA/CHMP/115147/2011, Dec. 16, 2010.
Giri et al., Pharmacokinetics and Metabolism of a Novel Antifibrotic Drug Pirfenidone, in Mice Following Intravenous Administration, Biopharm. Drug Dispos., 23, 203-211, 2002.
Intermune Core Presentation to the FDA Advisory Committee, Pirfenidone, Downloaded from http://www.fda.gov/downloads/AdvisoryCommittees/CommitteesMeetingMaterials/Drugs/Pulmonary-AllergyDrugsAdvisoryCommittee/UCM206399.pdf, Mar. 9, 2010.
Nakazato et al., A novel anti-fibrotic agent pirfenidone suppresses tumor necrosis factor-a lpha at the translational level, Eur. J. Pharmacol., 446, 177-185, 2002.
Oku et al., Pirfenidone suppresses tumor necrosis factor-alpha, enhances interleukin-10 and protects mice from endotoxic shock, Eur. J. Pharmacol., 446, 167-176, 2002.
Japanese Pharmaceuticals and Medical Devices Agency Review of Pirespa (Pirfenidone), Downloaded from http://www.pmda.go.jp/english/service/pdf/Pirespa-Pirfenidone.pdf, Sep. 8, 2008.
Food and Drug Administration, Transcript for the Mar. 9, 2010 Meeting of the Pulmonary-Allergy Drugs Advisory Committee, Downloaded from http://www.fda.gov/downloads/AdvisoryCommittees/CommitteesMeetingMaterials/Drugs/Pulmonary-AllergyDrugsAdvisoryCommittee/UCM208806.pdf, Mar. 9, 2010.
Tsuchiya et al., Pirfenidone prevents endotoxin-induced liver injury after partial hepatectomy in rats, J. Hepatol., 40, 94-101, 2004.
Wang et al., Protective effects of pirfenidone on D-galactosamine and lipopolysaccharide-induced acute hepatotoxicity in rats, Inflamm. Res., 57, 183-188, 2008.
Baillie, Thomas, The Use of Stable Isotopes in Pharmaceutical Research, Pharmacological Reviews, 33(2), 81-132, 1981.
Browne, Thomas; Stable Isotope Techniques in Early Drug Development: An Economic Evaluation, J. Clin.Pharmacol., 1998, 38, 213-220.
Cherrah et al.; Study of Deuterium Isotope Effects on Protein Binding by Gas Chromatography/Mass Spectrometry. Caffeine and Deuterated Isomers, Biomedical and Environmental Mass Spectrometry, 1987, 14, 653-657.
Dyck et al.; Effects of Deuterium Substitution on the Catabolism of Beta-Phenethylamine: An In Vivo Study, J. Neurochem., 1986, 46(2), 399-404.
Gouyette, Alain; Use of Deuterium-Labelled Elliptinium and Its Use in Metabolic Studies, Biomedical and Environmental Mass Spectrometry, 1988, 15, 243-247.
Haskins, N. J.; The Application of Stable Isotopes in Biomedical Research, Biomedical Mass Spectrometry, 1982, 9(7), 269-277.
Honma et al.; The Metabolism of Roxatidine Acetate Hydrochloride, Drug Metabolism and Disposition, 1987, 15(4), 551-559.
Pieiaszek et al.; Moricizine Bioavailability Via Simultaneous, Dual, Stable Isotope Administration: Bioequivalence Implications, J. Clin. Pharmacol., 1999, 39, 817-825.
Tonn et al.; Simultaneous Analysis of Diphenylhydramine and a Stable Isotope Analog (2H10) Diphenylhydramine Using Capillary Gas Chromatography With Mass Selective Detection in Biological Fluids From Chronically Instrumented Pregnant Ewes, Biomedical Mass Spectrometry, 1993, 22, 633-642.
Wolen et al.; The Application of Stable Isotopes to Studies of Drug Bioavailibility and Bioequivalence, J. Clin. Pharmacol., 1986, 26, 419-424.
Liu et al., Deuterated pirfenidone, Concert Pharmaceuticals, Inc., U.S. Appl. No. 12/283,290—Prosecution History, Downloaded Jan. 22, 2015.
EP 08771632—Prosecution History of the European Patent Office, Downloaded Jan. 22, 2015.
Westheimer, F.H., The Magnitude of the Primary Kinetic Isotope Effect for Compounds of Hydrogen and Deuterium, Chem. Rev., 61, 265-273, 1960.
Liu, Julie, F., Deuterated Pirfenidone, Concert Pharmaceuticals, Inc., WO 2009035598—International Preliminary Report on Patentability, Mar. 16, 2010.
Meanwell, N.A., Synopsis of Some Recent Tactical Application of Bioisosteres in Drug Design, J. Med. Chem., 2011, 54, 2529-2591.
Foster, A.B., Deuterium Isotope Effects in the Metabolism of Drugs and Xenobiotics: Implications for Drug Design, Adv. Drug Res., Academic Press, London, GB, vol. 14, Jan. 1, 1985, pp. 1-40.
Szajna et al., NMR Studies of Mononuclear Octahedral Ni(II) Complexes Supported by Tris(2-pyridyl)methyl)amine-Type Ligands, Inorganic Chemistry, 43(13), 3988-3997, 2004.
Wang et al., Simple Determination of Pirfenidone in Rat Plasma via High-Performance Liquid Chromatography, Biomed. Chromatogr., 2006, 20, 1375-1379.
Gant, T., Substituted N-Aryl Pyridinones as Fibrotic Inhibitors, NZ 599643 Notice of Acceptance, Auspex Pharmaceutical, Inc., Nov. 7, 2013.
Gant, T., Substituted N-Aryl Pyridinones as Fibrotic Inhibitors, U.S. Appl. No. 12/143,484—Prosecution History, Auspex Pharmaceutical, Inc., Downloaded Jan. 22, 2015.
Gant, T., Substituted N-Aryl Pyridinones as Fibrotic Inhibitors, NZ 599643 Examination Report, Auspex Pharmaceutical, Inc., Apr. 30, 2012.
Gant, T., Substituted N-Aryl Pyridinones as Fibrotic Inhibitors, CN 200880102512.1 Examination Report, Auspex Pharmaceutical, Inc., Feb. 1, 2012.
Gant, T., Substituted N-Aryl Pyridinones as Fibrotic Inhibitors, NZ 582134 Examination Report, Auspex Pharmaceutical, Inc., Oct. 27, 2010.
Gant, T., Substituted N-Aryl Pyridinones as Fibrotic Inhibitors, U.S. Appl. No. 13/663,188—Prosecution History, Auspex Pharmaceutical, Inc., Downloaded Jan. 22, 2015.
Gant, T., Substituted N-Aryl Pyridinones as Fibrotic Inhibitors, U.S. Appl. No. 14/132,528—Prosecution History, Auspex Pharmaceutical, Inc., Downloaded Jan. 22, 2015.
Gant, T., Substituted N-Aryl Pyridinones as Fibrotic Inhibitors, U.S. Appl. No. 14/266,048—Prosecution History, Auspex Pharmaceutical, Inc., Downloaded Jan. 22, 2015.
Gant, T., Deuterated pirfenidone, U.S. Appl. No. 13/431,290—Prosecution History, Auspex Pharmaceutical, Inc., Downloaded Jan. 22, 2015.
Gant, T., Substituted N-Aryl Pyridinones as Fibrotic Inhibitors, U.S. Appl. No. 14/455,339—Prosecution History, Auspex Pharmaceutical, Inc., Downloaded Jan. 22, 2015.
Gant, T., Substituted N-Aryl Pyridinones as Fibrotic Inhibitors, AU 2008265595 Examination Report, Auspex Pharmaceutical, Inc., Jun. 3, 2013.

(56) References Cited

OTHER PUBLICATIONS

Gant, T., Substituted N-Aryl Pyridinones as Fibrotic Inhibitors, AU 2008265595 Response to Examination Report, Auspex Pharmaceutical, Inc., Oct. 30, 2014.

Gant, T., Substituted N-Aryl Pyridinones as Fibrotic Inhibitors, CA 2691379 Office Action, Auspex Pharmaceutical, Inc., Jan. 13, 2014.

Gant, T., Substituted N-Aryl Pyridinones as Fibrotic Inhibitors, CA 2691379 Response to Office Action, Auspex Pharmaceutical, Inc., Jul. 14, 2014.

Gant, T., Substituted N-Aryl Pyridinones as Fibrotic Inhibitors, CN 20088010251 Decision of Rejection, Auspex Pharmaceutical, Inc., Aug. 22, 2013.

Gant, T. Substituted N-Aryl Pyridinones as Fibrotic Inhibitors, CN 200880102512 Second Examination Report, Auspex Pharmaceutical, Inc., Dec. 21, 2012.

Gant, T., Substituted N-Aryl Pyridinones as Fibrotic Inhibitors, IL 202840 First Office Action, Auspex Pharmaceutical, Inc., Nov. 4, 2012.

Gant, T., Substituted N-Aryl Pyridinones as Fibrotic Inhibitors, IL 202840 First Office Action Remarks, Auspex Pharmaceutical, Inc., Jun. 10, 2013.

Gant, T., Substituted N-Aryl Pyridinones as Fibrotic Inhibitors, IL 202840 Second Office Action, Auspex Pharmaceutical, Inc., Aug. 5, 2013.

Gant, T., Substituted N-Aryl Pyridinones as Fibrotic Inhibitors, IL 202840 Application as Allowed, Auspex Pharmaceutical, Inc., Jun. 5, 2014.

Gant, T., Substituted N-Aryl Pyridinones as Fibrotic Inhibitors, JP 2010513457 First Office Action, Auspex Pharmaceutical, Inc., Jun. 21, 2013.

Gant, T., Substituted N-Aryl Pyridinones as Fibrotic Inhibitors, JP 2010513457 First Office Action Remarks and Amended Claims, Auspex Pharmaceutical, Inc., Dec. 6, 2013.

Gant, T., Substituted N-Aryl Pyridinones as Fibrotic Inhibitors, JP 2010513457 Notice of Grant, Auspex Pharmaceutical, Inc, Jun. 26, 2014.

Gant, T., Substituted N-Aryl Pyridinones as Fibrotic Inhibitors, NZ 599643 Examination Report, Auspex Pharmaceutical, Inc, Apr. 30, 2012.

Gant, T., Substituted N-Aryl Pyridinones as Fibrotic Inhibitors, NZ 599643 Response to Examination Report, Auspex Pharmaceutical, Inc., Oct. 25, 2013.

* cited by examiner

SUBSTITUTED N-ARYL PYRIDINONES

This application claims the benefit of priority of U.S. provisional application No. 61/450,489, filed Mar. 8, 2011, the disclosure of which is hereby incorporated by reference as if written herein in its entirety.

FIELD

The present invention is directed to substituted N-Aryl pyridinones, pharmaceutically acceptable salts and prodrugs thereof, the chemical synthesis thereof, and medical use of such compounds for the treatment and/or management of idiopathic pulmonary fibrosis, uterine fibroids, multiple sclerosis, renal fibrosis, diabetic kidney disease, endotoxin-induced liver injury after partial hepatectomy or hepatic ischemia, allograft injury after organ transplantation, cystic fibrosis, atrial fibrilation, neutropenia, scleroderma, dermatomyositis, cirrhosis, diffuse parenchymal lung disease, mediastinal fibrosis, tuberculosis, spleen fibrosis caused by sickle-cell anemia, rheumatoid arthritis, and/or any disorder ameliorated by modulating fibrosis and/or collagen infiltration into tissues.

BACKGROUND

Pirfenidone (Deskar®, Esbriet™, Pirespa, AMR-69, F-647, S-7701), 5-methyl-1-phenyl-1H-pyridin-2-one, is an orally administered antifibrotic agent. Pirfenidone is effective in rodent disease models. Pirfenidone inhibits DNA synthesis in leiomyoma cells and myometrial cells (Lee et al, *Journal of Clinical Endocrinology and Metabolism* 1998, 83(1), 219-23). Pirfenidone has been approved for the treatment of idiopathic pulmonary fibrosis (IPF) in Japan and received positive opinion from CHMP in Europe.

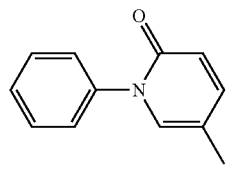

Pirfenidone

While the chemical structure of pirfenidone is relatively simple, the metabolism is only partially understood. For example, the methyl group is thought to be susceptible to oxidation which would lead to a corresponding hydroxymethyl metabolite, "M1." M1 is thought to be further oxidized to a carboxylic acid metabolite, "M2" (Wang et al, *Biomedical Chromatography* 2006, 20, 1375-1379). A third detected metabolite is believed to be a phase II product possibly originating from M1 or M2. Pirfenidone has a very short half-life in humans and will likely be dosed at more than once per day.

The most common adverse reactions or events associated with pirfenidone therapy include gastrointestinal upset, nausea, fatigue, somnolence, dizziness, headache, and photosensitivity rash. Many of these effects can interfere with everyday activities and quality of life. These effects appear to be dose related. The adverse reactions associated with pirfenidone therapy are exacerbated when pirfenidone is administered at these higher doses.

Abnormal liver function is an additional adverse event that may be associated with or increase the hazards of pirfenidone therapy. Abnormal liver function may manifest as abnormalities in levels of biomarkers of liver function, including alanine transaminase, aspartate transaminase, bilirubin, and/or alkaline phosphatase, and may be an indicator of drug-induced liver injury. See *FDA Draft Guidance for Industry. Drug-Induced Liver Injury: Premarketing Clinical Evaluation*, October 2007.

Currently, adverse events following administration of pirfenidone are alleviated by dose reduction or discontinuation of pirfenidone. In a recent study, for adverse events rated Grade 2 or worse, the dosage was reduced in a stepwise manner: from 9 tablets per day to 6 tablets per day and 6 tablets per day to 3 tablets per day. Azuma et al., *Am. J. Respir. Crit. Care Med.*, 2005, 171, 1040-47. If, after a period of 14 days of observation with reduced dosage, the adverse event persisted or increased, the dosage was further reduced by one more step—from 6 tablets per day to 3 tablets per day. If the adverse event persisted or increased despite reducing the dosage to 3 tablets per day, the study medication was discontinued.

There remains an unmet clinical need for a method of administering higher doses of pirfenidone to a patient in a manner that eliminates or minimizes adverse events, such as abnormal liver function, nausea, vomiting, gastrointestinal upset, drowsiness, dizziness, headache, somnolence, and other potentially dangerous side effects that can occur with pirfenidone therapy.

SUMMARY OF THE INVENTION

Disclosed herein is a d-pirfenidone compound having structural Formula I:

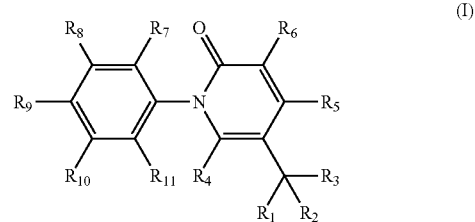

or a pharmaceutically acceptable salt, solvate, or prodrug thereof; wherein:

$R_1, R_2, R_3, R_4, R_5, R_6, R_7, R_8, R_9, R_{10}$, and $R_{11}$ are selected from the group consisting of hydrogen or deuterium; and at least one $R_1, R_2, R_3, R_4, R_5, R_6, R_7, R_8, R_9, R_{10}$, and $R_{11}$ is deuterium; and In certain embodiments if $R_7, R_8, R_9, R_{10}$, and $R_{11}$ are deuterium, then at least one of $R_1, R_2, R_3, R_4, R_5$, and $R_6$ is deuterium.

In an embodiment, a method of reducing the likelihood of adverse events in a patient receiving d-pirfenidone therapy wherein the d-pirfenidone is in the form of a pharmaceutical composition is disclosed. The method comprises, for example, administering a therapeutically effective amount of d-pirfenidone to a patient with food. In certain embodiments, the d-pirfenidone is $d_3$-pirfenidone.

In an embodiment, a method of reducing the likelihood of somnolence in a patient receiving d-pirfenidone therapy wherein the d-pirfenidone is in the form of a pharmaceutical composition is disclosed. The method comprises, for example, administering a therapeutically effective amount of d-pirfenidone to the patient with food. In certain embodiments, the d-pirfenidone is $d_3$-pirfenidone.

In an embodiment, a method of reducing the likelihood of nausea in a patient receiving d-pirfenidone therapy wherein the d-pirfenidone is in the form of a pharmaceutical composition is disclosed. The method comprises, for example, administering a therapeutically effective amount of d-pirfenidone to the patient with food. In certain embodiments, the d-pirfenidone is $d_3$-pirfenidone.

In an embodiment, a method of reducing the likelihood of headaches in a patient receiving d-pirfenidone therapy wherein the d-pirfenidone is in the form of a pharmaceutical composition is disclosed. The method comprises, for example, administering a therapeutically effective amount of d-pirfenidone to the patient with food. In certain embodiments, the d-pirfenidone is $d_3$-pirfenidone.

In some embodiments, the likelihood of one or more adverse effects is reduced. For example, in some embodiments, the likelihood of nausea and somnolence is reduced. In other embodiments, the likelihood of nausea and headaches is reduced. In still other embodiments, the likelihood of somnolence and headaches is reduced. In some embodiments, the likelihood of nausea, somnolence and headaches is reduced.

In some embodiments, the methods comprise administering d-pirfenidone to a patient, wherein the administering comprises providing d-pirfenidone in about 100 milligrams to about 400 milligrams per unit dosage form. In some embodiments, the administering comprises providing one or more unit dosage forms one or more times per day to the patient. In an embodiment, the administering comprises providing one or more capsules comprising d-pirfenidone one or more times per day to the patient. In certain embodiments, the d-pirfenidone is $d_3$-pirfenidone.

In some embodiments, the food is a solid food with sufficient caloric and fat content that it is not rapidly dissolved and absorbed in the stomach. Thus, in some embodiments, the food is a meal, for example, breakfast, lunch or dinner.

In some embodiments, the therapeutically effective amount of d-pirfenidone is administered to the patient between about 1 hour prior to about 2 hours after eating a meal. In some embodiments, the d-pirfenidone is administered to the patient within about 30 minutes, about 15 minutes of consuming food. In certain embodiments, the d-pirfenidone is $d_3$-pirfenidone.

In some embodiments, the methods disclosed herein further comprise providing information to prescribing physicians and patients receiving d-pirfenidone therapy useful for decreasing adverse events when taking d-pirfenidone. In preferred embodiments, the methods further comprise advising a patient to take d-pirfenidone with food. In some embodiments, the methods further comprise advising a patient to take d-pirfenidone with food to avoid and/or minimize adverse events associated with d-pirfenidone therapy. In certain embodiments, the d-pirfenidone is $d_3$-pirfenidone.

In some embodiments, the methods include providing the composition to the patient in a container associated with printed labeling advising that the administration with food results in a reduction in the likelihood of adverse events. In some embodiments, the methods include providing the pharmaceutical composition to the patient in a container associated with printed labeling advising the patient that the pharmaceutical composition is to be, administered between about 1 hour prior to consuming food to about 2 hours after consuming food. In some embodiments, the methods include providing the pharmaceutical composition to the patient in a container associated with printed labeling advising the patient that the pharmaceutical composition is to be administered at substantially the same time as consuming food.

Another embodiment provides an article of manufacture or a kit comprising a container, wherein the container holds a pharmaceutical composition comprising d-pirfenidone in unit dosage form, and printed labeling instructions advising of the varying side effects when the composition is taken with and without food. In some embodiments, the printed instructions advise the patient to take the composition with food if stomach upset or somnolence occurs. In certain embodiments, the d-pirfenidone is $d_3$-pirfenidone.

In some embodiments, the printed instructions further advise the patient that the administration of the composition with food results in a reduction in the likelihood of adverse events. In some embodiments, the printed instructions advise the patient to take the composition between about 1 hour prior to consuming food to about 2 hours after consuming food. In some embodiments, the printed instructions advise the patient to take the composition at substantially the same time as consuming food. In some embodiments, the printed instructions advise the patent to take the composition between about 30 minutes prior to about 2 hours after consuming food. In some embodiments, the printed instructions advise the patient to take the composition immediately after the consumption of food up to 1 hour after said consumption. In some embodiments, the printed instructions advise the patient to take the composition with a meal.

In some embodiments, the printed instructions advise the patient to take one or more of the capsules twice per day. In some embodiments, the printed instructions advise the patient to take one or more capsules two or three times per day.

In another embodiment, a method for providing d-pirfenidone therapy to a patient is disclosed, comprising providing a therapeutic dose of d-pirfenidone to the patient, and advising the patient to take the d-pirfenidone with food. In certain embodiments, the d-pirfenidone is $d_3$-pirfenidone.

Another disclosed embodiment is a method for providing d-pirfenidone therapy to a patient, comprising providing a therapeutic dose of d-pirfenidone to the patient, and advising the patient that consuming the d-pirfenidone with food may reduce the incidence of adverse events resulting from d-pirfenidone therapy. In certain embodiments, the d-pirfenidone is $d_3$-pirfenidone.

Also disclosed is a method for providing d-pirfenidone therapy to a patient, comprising providing a therapeutic dose of d-pirfenidone to the patient; and advising the patient that consuming the d-pirfenidone with food reduces mean maximum plasma concentration of d-pirfenidone. In certain embodiments, the d-pirfenidone is $d_3$-pirfenidone.

In some embodiments, the food is a solid food with sufficient bulk and fat content that it is not rapidly dissolved and absorbed in the stomach. In certain embodiments, the food is a meal, such as breakfast, lunch, or dinner. In some embodiments, the food is at least about 100 calories, about 200 calories, about 250 calories, about 300 calories, about 400 calories, about 500 calories, about 600 calories, about 700 calories, about 800 calories, about 900 calories, about 1000 calories, about 1250 calories, or about 1500 calories.

The methods disclosed herein include administering d-pirfenidone to a patient with food. The d-pirfenidone can be administered any time of day with food. For example, in some embodiments, the food can be consumed at any time during the period between from about 2 hours prior to the administration of d-pirfenidone to about 2 hours after the administration of d-pirfenidone. In some embodiments, the food can be consumed within the time period of about 2 hours, about 1.5 hours, about 1 hour, about 45 minutes, about 30 minutes, about 15 minutes, about 10 minutes, or about 5 minutes prior to the administration of d-pirfenidone. In some embodiments, the food can be consumed within the time period of about 5 minutes, about 10 minutes, about 15 minutes, about 30 minutes, about 45 minutes, about 1 hour, about 1.5 hours, or about 2 hours after the administration of d-pirfenidone. In some embodiments, the administration of d-pirfenidone to the patient is immediately after the consumption of food (e.g., within about 1 minute after food consumption) up to about 1 hour after food consumption. In some embodiments, d-pirfenidone is administered at substantially the same time as the consumption of the food. In certain embodiments, the d-pirfenidone is $d_3$-pirfenidone.

In some embodiments, an effective daily intake of d-pirfenidone is between about 100 mg and about 200 mg per day, about 200 mg and about 300 mg per day, about 300 mg and about 400 mg per day, about 400 mg and about 500 mg per day, about 500 mg and about 600 mg per day, about 600 mg and about 700 mg per day, about 700 mg and about 800 mg per day, about 800 mg and about 900 mg per day, about 900 mg and about 1000 mg per day, about 1000 mg and about 1100 mg per day, about 1100 mg and about 1200 mg per day, about 1200 mg and about 1300 mg per day, about 1300 mg and about 1400 mg per day, about 1400 mg and about 1500 mg per day, about 1500 mg and about 1600 mg per day, about 1600 mg and about 1700 mg per day, about 1700 mg and about 1800 mg per day, about 1800 mg and about 1900 mg per day, about 1900 mg and about 2000 mg per day, about 2000 mg and about 2100 mg per day, about 2100 mg and about 2200 mg per day, about 2200 mg and about 2300 mg per day, about 2300 mg and about 2400 mg per day, about 2400 mg and about 2500 mg per day, about 2500 mg and about 2600 mg per day, about 2600 mg and about 2700 mg per day, about 2700 mg and about 2800 mg per day, about 2800 mg and about 2900 mg per day, about 2900 mg and about 3000 mg per day, about 3000 mg and about 3100 mg per day, about 3100 mg and about 3200 mg per day, about 3200 mg and about 3300 mg per day, about 3300 mg and about 3400 mg per day, about 3400 mg and about 3500 mg per day, about 3500 mg and about 3600 mg per day, about 3600 mg and about 3700 mg per day, about 3700 mg and about 3800 mg per day, about 3800 mg and about 3900 mg per day, or about 3900 mg and about 4000 mg per day. In certain embodiments, the d-pirfenidone is $d_3$-pirfenidone.

In an embodiment, d-pirfenidone is administered to the subject in a unit dosage form comprising about 100 to about 400 mg of d-pirfenidone per unit. In certain embodiments, the d-pirfenidone is $d_3$-pirfenidone.

The dosing may be once or twice or three times daily, with one or more units per dose. In some embodiments, the effective daily intake of d-pirfenidone is administered as one, two, three, four, five, six, or more doses administered separately at appropriate intervals throughout the day. In some embodiments, each dose comprises one, two, three or more unit dosage forms. For example, in some embodiments, one or more units are administered to the subject one or more times per day. In some embodiments, one or more units are administered to the subject twice per day. In some embodiments, one or more units are administered to the subject two or three times per day. In some embodiments, 3 units are administered two or three times per day. In some embodiments, d-pirfenidone is administered as multiple doses spaced throughout the day and each dose comprises a therapeutically effective amount of d-pirfenidone. In some embodiments, d-pirfenidone is administered with food once per day. In certain embodiments, the d-pirfenidone is $d_3$-pirfenidone.

In general the daily intake will be in the range of about 100 mg/day to about 10 g/day, or about 200 mg to about 5 g/day, or about 400 mg to about 3 g/day, or about 500 mg to about 2 g/day, in single, divided, or continuous doses for a patient weighing between about 40 to about 100 kg (which doses may be adjusted for patients above or below this weight range, particularly children under 40 kg). Generally the daily intake will be in the range of about 25 mg/kg to about 200 mg/kg of body weight per day. In some embodiments, the maximum daily intake of d-pirfenidone is 4 g/day.

The exact dosage will typically be determined by the practitioner, in light of factors related to the subject that requires treatment. Dosage and administration are generally adjusted to provide sufficient levels of d-pirfenidone or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The specifications for the unit dosage forms described herein depend on the particular dose employed and the effect to be achieved, and the pharmacodynamics associated with d-pirfenidone in the host.

The decrease in duration or number of adverse events in a patient receiving d-pirfenidone therapy can be evidenced in any suitable manner. Desirably, the oral administration of d-pirfenidone with food results in a reduction in the frequency and/or severity of adverse events as evidenced by a review of adverse events following administration of d-pirfenidone as compared to the administration of d-pirfenidone without food. In certain embodiments, the d-pirfenidone is $d_3$-pirfenidone.

In some embodiments, d-pirfenidone is provided to a patient in a container associated with prescribing information that advises the patient to take the pharmaceutical composition with food, and in some embodiments further advises the patient that taking the composition with food results in a reduction in the duration, likelihood, and/or severity of adverse events associated with d-pirfenidone therapy. In some embodiments, the prescribing information advises the patient to take the composition with food if stomach upset and/or somnolence occurs. In certain embodiments, the d-pirfenidone is $d_3$-pirfenidone.

In some embodiments, the methods can include identifying a subject at risk for or suffering from an adverse event associated with d-pirfenidone therapy and administering a therapeutically effective amount of d-pirfenidone with food. In certain embodiments, the d-pirfenidone is $d_3$-pirfenidone.

In an embodiment, the methods include identifying a patient who could benefit from the methods disclosed herein. In some embodiments, the methods described herein include identifying a subject who has experienced or is experiencing an adverse event, such as gastrointestinal symptoms, somnolence, and/or headache, following administration of d-pirfenidone. Identifying such subjects may be accomplished by any means that indicates a subject who may benefit from the methods disclosed herein, for example, by clinical diagnosis, laboratory testing, or any other means known to one of skill in the art, including any combination of means for identification. In certain embodiments, the d-pirfenidone is $d_3$-pirfenidone.

The methods described herein include preventing, alleviating, and/or minimizing the duration and/or severity of adverse events associated with d-pirfenidone therapy. In certain embodiments, the d-pirfenidone is $d_3$-pirfenidone.

In an embodiment, the methods disclosed herein result in a reduction in the likelihood of nausea in patients receiving d-pirfenidone therapy with food (fed) as compared to patients receiving d-pirfenidone therapy without food (fasted). In certain embodiments, the likelihood of nausea of a fed population is reduced by at least about 25% relative to the likelihood of nausea of a fasted population; in further embodiments, the likelihood of nausea is reduced by at least about 30%; in further embodiments, reduced by at least about 33%; in further embodiments, reduced by at least about 40%; in further embodiments, reduced by at least about 50%; in further embodiments, reduced by at least about 60%; in further embodiments, reduced by at least 70%; and in further embodiments, reduced by at least about 75%. Likelihood of nausea may be measured by any reproducible means of measurement. In certain embodiments, the d-pirfenidone is $d_3$-pirfenidone.

In an embodiment, the methods disclosed herein result in a reduction in the likelihood of somnolence in patients receiving d-pirfenidone therapy with food (fed) as compared to patients receiving d-pirfenidone therapy without food (fasted). In certain embodiments, the likelihood of somnolence of a fed population is reduced by at least about 25% relative to the likelihood of somnolence of a fasted population; in further embodiments, the likelihood of somnolence is reduced by at least about 30%; in further embodiments, reduced by at least about 33%; in further embodiments, reduced by at least about 40%; in further embodiments, reduced by at least about 50%; in further embodiments, reduced by at least about 60%; in further embodiments, reduced by at least 70%; and in further embodiments, reduced by at least about 75%. Likelihood of somnolence may be measured by any reproducible means of measurement. In certain embodiments, the d-pirfenidone is $d_3$-pirfenidone.

In an embodiment, the methods disclosed herein result in a reduction in the likelihood of headache in patients receiving d-pirfenidone therapy with food (fed) as compared to patients receiving d-pirfenidone therapy without food (fasted). In certain embodiments, the likelihood of headache of a fed population is reduced by at least about 25% relative to the likelihood of headache of a fasted population; in further embodiments, the likelihood of headache is reduced by at least about 30%; in further embodiments, reduced by at least about 33%; in further embodiments, reduced by at least about 40%; in further embodiments, reduced by at least about 50%; in further embodiments, reduced by at least about 60%; in further embodiments, reduced by at least about 70%; and in further embodiments, reduced by at least about 75%. Likelihood of headache may be measured by any reproducible means of measurement. In certain embodiments, the d-pirfenidone is $d_3$-pirfenidone.

In an embodiment, the methods disclosed herein result in a reduction in the likelihood of dizziness in patients receiving d-pirfenidone therapy with food (fed) as compared to patients receiving d-pirfenidone therapy without food (fasted). In certain embodiments, the likelihood of dizziness of a fed population is reduced by at least about 25% relative to the likelihood of dizziness of a fasted population; in further embodiments, the likelihood of dizziness is reduced by at least about 30%; in further embodiments, reduced by at least about 33%; in further embodiments, reduced by at least about 40%; in further embodiments, reduced by at least about 50%; in further embodiments, reduced by at least about 60%; in further embodiments, reduced by at least 70%; and in further embodiments, reduced by at least about 75% Likelihood of dizziness may be measured by any reproducible means of measurement. In certain embodiments, the d-pirfenidone is $d_3$-pirfenidone.

Also disclosed is a method for providing d-pirfenidone therapy to a patient, comprising providing a therapeutic dose of d-pirfenidone (usually contained within a pharmaceutical composition) to the patient; and advising the patient that consuming the d-pirfenidone with food significantly reduces mean maximum plasma concentration ($C_{max}$) of d-pirfenidone and/or significantly increases (makes longer) the mean absorption half life ($t_{1/2}$, abs) of d-pirfenidone in comparison to consuming the d-pirfenidone without food. In certain embodiments, the d-pirfenidone is consumed within one hour or 30 minutes of the food consumption. In some embodiments, the d-pirfenidone is consumed at the same time as the food consumption. In other embodiments, the d-pirfenidone is consumed during the time period from one hour prior to food consumption to two hours after food consumption. In certain embodiments, the d-pirfenidone is $d_3$-pirfenidone.

In some embodiments, the patient may be advised that consuming d-pirfenidone with food significantly reduces mean maximum plasma concentration of d-pirfenidone such that the ratio of the average $C_{max}$ for the fed patient to the average $C_{max}$ of the fasted patient ($C_{max(fed)}$:$C_{max(fasted)}$) ranges from about 0.3 to about 0.8, about 0.35 to about 0.75, about 0.4 to about 0.7, about 0.4 to about 0.6, about 0.4 to about 0.5, or about 0.45 to about 0.55. In certain embodiments, the d-pirfenidone is $d_3$-pirfenidone.

Additionally or alternatively, in some embodiments, the patient may be advised that consuming d-pirfenidone with food significantly increases mean absorption half life of the d-pirfenidone such that the ratio of mean $t_{1/2,abs}$ of the fed patient to mean $t_{1/2,abs}$ of the fasted patient ($t_{1/2,abs(fed)}$:$t_{1/2,abs\ (fasted)}$) ranges from about 1.5 to about 5, about 1.75 to about 4.5, about 2 to about 4, about 2.5 to about 3.5, about 2.75 to about 3.5, or about 2.75 to 3.25. In a specific embodiment, the mean $t_{1/2,abs}$ increases from 0.572 hours without food to 1.78 hours with food. In certain embodiments, the d-pirfenidone is $d_3$-pirfenidone.

In some embodiments, the patient may be advised that consuming d-pirfenidone with food maintains at least 10%, at least 20%, at least 30%, at least 40%, at least 50%, at least 60%, at least 70%, or 80% of the overall mean absorption of d-pirfenidone in comparison to consuming d-pirfenidone without food, as measured by the Area Under the Curve (AUC) of an absorption profile. In certain embodiments, the d-pirfenidone is $d_3$-pirfenidone.

In all the embodiments, it is contemplated that the patient may be advised in writing or orally, and that the written information may be contained (for example) in a label, a sticker, a product insert, product information, or prescribing information.

In related embodiments, the invention provides a method for administering d-pirfenidone to a human patient in need thereof, e.g. a patient suffering from pulmonary fibrosis, comprising administering a pharmaceutical composition comprising a therapeutic dose of d-pirfenidone with food to the patient, wherein the mean maximum plasma concentration ($C_{max}$) of d-pirfenidone is significantly reduced and/or the mean absorption half life ($t_{1/2,abs}$) of d-pirfenidone is significantly longer. In some embodiments, the ratio of the average $C_{max}$ for the fed patient to the average $C_{max}$ of the fasted patient ($C_{max(fed)}$:$C_{max(fasted)}$) ranges from about 0.3 to about 0.8, about 0.35 to about 0.75, about 0.4 to about 0.7, about 0.4 to about 0.6, about 0.4 to about 0.5, or about 0.45 to about 0.55, or about 0.5, and/or wherein the ratio of mean $t_{1/2,abs}$ of the fed patient to mean $t_{1/2,abs}$ of the fasted patient ($t_{1/2,abs(fed)}$:$t_{1/2,abs(fasted)}$) ranges from about 1.5 to about 5, about 1.75 to about 4.5, about 2 to about 4, about 2.5 to about 3.5, about 2.75 to about 3.5, or about 2.75 to 3.25, or about 3. In certain embodiments, the d-pirfenidone is $d_3$-pirfenidone.

For fed conditions, the $C_{max}$ is typically lower that the $C_{max}$ of d-pirfenidone under fasted conditions. In some embodiments, the ratio of $C_{max(fed)}$ to $C_{max(fasted)}$ is about 0.3 to about 0.8, about 0.35 to about 0.7, about 0.4 to about 0.65, about 0.4 to about 0.6, about 0.45 to about 0.65, or about 0.45 to about 0.55. In specific embodiments, the ratio of $C_{max(fed)}$ to $C_{max(fasted)}$ is about 0.5. In certain embodiments, the d-pirfenidone is $d_3$-pirfenidone.

The absorption half life of d-pirfenidone when administered under fed conditions ($t_{1/2,abs\ (fed)}$) is typically longer than the absorption half life of d-pirfenidone when administered under fasted conditions ($t_{1/2,abs(fasted)}$). In some embodiments, the ratio $t_{1/2,abs(fed)}$ to $t_{1/2,abs(fasted)}$ ($t_{1/2,abs(fed)}$:$t_{1/2,abs(fasted)}$) is about 1.5 to about 5, about 2 to about 4, or about 2.5 to about 3.5, about 2.75 to about 3.5, or about 2.75 to 3.25. In specific embodiments, $t_{1/2,abs(fed)}$:$t_{1/2,abs(fasted)}$ is about 2, about 2.5, about 3, about 3.5, about 4, about 4.5, or about 5. In certain embodiments, the d-pirfenidone is $d_3$-pirfenidone.

The total absorption of d-pirfenidone under fed or fasted conditions can also be determined by comparing the area under the curve (AUC) of the absorption curves. In some embodiments, the $AUC_{fed}$ is at least about 10%, 20%, 30%, 40%, 50%, 60%, 70%, 80%, or at least about 90% that of $AUC_{fasted}$. In certain embodiments, the d-pirfenidone is $d_3$-pirfenidone.

One aspect of the invention provides methods for administering a therapeutically effective dose of d-pirfenidone to a patient that has exhibited abnormal biomarkers of liver function after d-pirfenidone administration for the treatment of fibrosis, e.g. idiopathic pulmonary fibrosis (IPF). In some embodiments, a patient is identified who exhibits a significantly abnormal level of one, two, three or more biomarkers of liver function, e.g. the level of a Grade 2 abnormality, after administration of an original full target dose of d-pirfenidone. In such patients, the dose of d-pirfenidone is reduced or discontinued until levels of the abnormal biomarkers approach or are within normal range, after which patients are administered increasing doses of d-pirfenidone, up to the original full target dose. Alternatively, the dose of d-pirfenidone is not reduced at all, but liver biomarkers continue to be monitored. In another embodiment, after an optional temporary dose reduction or discontinuation, patients are administered d-pirfenidone at a permanently reduced dose. As used herein, "original full target dose" means the therapeutically effective dose approved by the U.S. Food and Drug Administration or a similar agency in a foreign country, optionally other than Japan. The total daily dose is administered one, two or three times per day. In certain embodiments, the d-pirfenidone is $d_3$-pirfenidone.

In some embodiments of the methods, d-pirfenidone is administered to a patient exhibiting a liver function Grade 2 abnormality as follows: (a) administering a reduced dosage of d-pirfenidone for about one week, or until the liver function biomarkers return to Grade 0 or Grade 1, and (b) administering the original full target dose for at least one week, two weeks, three weeks, four weeks or a month, two months, or three months, or one year, or two years, or three years, or four years, or five years, or seven years, or ten years. In certain embodiments, the total daily dose is administered two or three times per day, with food. In certain embodiments, the d-pirfenidone is $d_3$-pirfenidone.

In some embodiments of the methods, d-pirfenidone is administered to a patient exhibiting a liver function Grade 2 abnormality as follows: (a) administering a first reduced dose of d-pirfenidone for about one week, or until the liver function biomarkers return to Grade 0 or Grade 1, (b) administering a second reduced dose of d-pirfenidone for about one week, and (c) administering the original full target dose for a time period of at least one week, two weeks, three weeks, four weeks or a month, two months, or three months, or one year, or two years, or three years, or four years, or five years, or seven years, or ten years. In certain embodiments, the total daily dose is administered two or three times per day, with food. In certain embodiments, the d-pirfenidone is $d_3$-pirfenidone.

In some embodiments of the methods, d-pirfenidone is administered to a patient exhibiting a liver function Grade 2 abnormality as follows: (a) discontinuing d-pirfenidone for about one week, or until the liver function biomarkers return to Grade 0 or Grade 1, (b) administering a first reduced dose of d-pirfenidone for about one week, (c) administering a second reduced dose of d-pirfenidone for about one week, and (d) administering the original full target dose for a time period of at least one week, two weeks, three weeks, four weeks or a month, two months, or three months, or one year, or two years, or three years, or four years, or five years, or seven years, or ten years. In certain embodiments, the total daily dose is administered two or three times per day, with food. In certain embodiments, the d-pirfenidone is $d_3$-pirfenidone.

Alternatively, d-pirfenidone is administered to a patient exhibiting a liver function Grade 2 abnormality at a permanently reduced dose. In some embodiments, d-pirfenidone is administered to a patient exhibiting a liver function Grade 2 abnormality as follows: administering a reduced dose of d-pirfenidone for a time period of at least one week, two weeks, three weeks, four weeks or a month, two months, or three months, or one year, or two years, or three years, or four years, or five years, or seven years, or ten years. In some embodiments, d-pirfenidone is administered to a patient exhibiting a liver function Grade 2 abnormality as follows: (a) administering a first reduced dose of d-pirfenidone for about a week, or until biomarkers of liver function are within normal limits, and (b) administering a second reduced dose of d-pirfenidone to the patient for a time period of at least one week, two weeks, three weeks, four weeks or a month, two months, or three months, or one year, or two years, or three years, or four years, or five years, or seven years, or ten years. In certain embodiments, the d-pirfenidone is $d_3$-pirfenidone.

In other embodiments, d-pirfenidone is administered to a patient exhibiting a liver function Grade 2 abnormality as follows: (a) discontinuing d-pirfenidone for about one week, or until the liver function biomarkers return to Grade 0 or Grade 1, (b) administering a first reduced dose of d-pirfenidone for about a week, or until biomarkers of liver function are within normal limits, and (c) administering a second reduced dose of d-pirfenidone to the patient for a time period of at least one week, two weeks, three weeks, four weeks or a month, two months, or three months, or one year, or two years, or three years, or four years, or five years, or seven years, or ten years. In still other embodiments, d-pirfenidone is administered to a patient exhibiting a liver function Grade 2 abnormality as follows: (a) discontinuing d-pirfenidone for about one week, or until the liver function biomarkers return to Grade 0 or Grade 1, and (b) administering a reduced dose of d-pirfenidone to the patient for a time period of at least one week, two weeks, three weeks, four weeks or a month, two months, or three months, or one year, or two years, or three years, or four years, or five years, or seven years, or ten years. In certain embodiments, the d-pirfenidone is $d_3$-pirfenidone.

In some embodiments of the methods, d-pirfenidone is administered to a patient exhibiting a liver function Grade 1 abnormality as follows: (a) administering a reduced dose of d-pirfenidone for a time period, optionally about one week, or until the liver function biomarkers return to Grade 0, and (b) administering the original full target dose for at least one week, two weeks, three weeks, four weeks or a month, two months, or three months, or one year, or two years, or three years, or four years, or five years, or seven years, or ten years. In certain embodiments, the total daily dose is administered two or three times per day, with food. In certain embodiments, the d-pirfenidone is $d_3$-pirfenidone.

In some embodiments of the methods, d-pirfenidone is administered to a patient exhibiting a liver function Grade 1 abnormality as follows: (a) administering a first reduced dose of d-pirfenidone for a time period, optionally about one week, or until the liver function biomarkers return to Grade 0, (b) administering a second reduced dose of d-pirfenidone for a time period, optionally about one week, and (c) administering the original full target dose for a time period of at least one week, two weeks, three weeks, four weeks or a month, two months, or three months, or one year, or two years, or three years, or four years, or five years, or seven years, or ten years. In certain embodiments, the total daily dose is administered two or three times per day, with food. In certain embodiments, the d-pirfenidone is $d_3$-pirfenidone.

In some embodiments of the methods, d-pirfenidone is administered to a patient exhibiting a liver function Grade 1 abnormality as follows: (a) discontinuing d-pirfenidone for a time period, optionally about one week, or until the liver function biomarkers return to Grade 0, (b) administering a first reduced dose of d-pirfenidone for a time period, optionally about one week, (c) administering a second reduced dose of d-pirfenidone for a time period, optionally about one week, and (d) administering the original full target dose for a time period of at least one week, two weeks, three weeks, four weeks or a month, two months, or three months, or one year, or two years, or three years, or four years, or five years, or seven years, or ten years. In certain embodiments, the total daily dose is administered two or three times per day, with food. In certain embodiments, the d-pirfenidone is $d_3$-pirfenidone.

Alternatively, d-pirfenidone is administered at a permanently reduced dose. In some embodiments, d-pirfenidone is administered to a patient exhibiting a liver function Grade 1 abnormality as follows: administering a reduced dose of d-pirfenidone for a time period of at least one week, two weeks, three weeks, four weeks or a month, two months, or three months, or one year, or two years, or three years, or four years, or five years, or seven years, or ten years. In some embodiments, d-pirfenidone is administered to a patient exhibiting a liver function Grade 1 abnormality as follows: (a) administering a first reduced dose of d-pirfenidone for a time period, optionally about a week, or until biomarkers of liver function are within normal limits, and (b) administering a second reduced dose of d-pirfenidone to the patient for a time period of at least one week, two weeks, three weeks, four weeks or a month, two months, or three months, or one year, or two years, or three years, or four years, or five years, or seven years, or ten years. In certain embodiments, the d-pirfenidone is $d_3$-pirfenidone.

In other embodiments, d-pirfenidone is administered to a patient exhibiting a liver function Grade 1 abnormality as follows: (a) discontinuing d-pirfenidone for a time period, optionally about one week, or until the liver function biomarkers return to Grade 0, (b) administering a first reduced dose of d-pirfenidone for about a week, or until biomarkers of liver function are within normal limits, and (c) administering a second reduced dose of d-pirfenidone to the patient for a time period of at least one week, two weeks, three weeks, four weeks or a month, two months, or three months, or one year, or two years, or three years, or four years, or five years, or seven years, or ten years. In still other embodiments, d-pirfenidone is administered to a patient exhibiting a liver function Grade 1 abnormality as follows: (a) discontinuing d-pirfenidone for a time period, optionally about one week, or until the liver function biomarkers return to Grade 0, and (b) administering a reduced dose of d-pirfenidone to the patient for a time period of at least one week, two weeks, three weeks, four weeks or a month, two months, or three months, or one year, or two years, or three years, or four years, or five years, or seven years, or ten years. In certain embodiments, the d-pirfenidone is $d_3$-pirfenidone.

In any of the embodiments described herein, any of the reduced doses of d-pirfenidone may be administered for a time period of 2 days, 3 days, 4 days, 5 days, 6 days, one week, about two weeks, or until the level of at least one biomarker of liver function has returned to within normal limits, or until all biomarkers or liver function has returned to within normal limits. In certain embodiments, the d-pirfenidone is $d_3$-pirfenidone.

In any of the embodiments described herein, the patient can have fibrotic lesional tissue. Such a patient is a patient who would benefit from d-pirfenidone administration. In one embodiment, the patient is suffering from pulmonary fibrosis, idiopathic interstitial pneumonia, autoimmune lung diseases, benign prostate hypertrophy, coronary or myocardial infarction, atrial fibrillation, cerebral infarction, myocardiac fibrosis, musculoskeletal fibrosis, post-surgical adhesions, liver cirrhosis, renal fibrotic disease, fibrotic vascular disease, scleroderma, Hermansky-Pudlak syndrome, neurofibromatosis, Alzheimer's disease, diabetic retinopathy, and/or skin lesions. In one embodiment, the patient is suffering from lymph node fibrosis associated with HIV. In one embodiment, the patient is suffering from pulmonary fibrosis, or idiopathic pulmonary fibrosis. In another embodiment, the patient is a person who would benefit from d-pirfenidone administration, optionally with the proviso that the patient is not suffering from idiopathic pulmonary fibrosis. In certain embodiments, the d-pirfenidone is $d_3$-pirfenidone.

In some embodiments, the biomarker of liver function is alanine transaminase, aspartate transaminase, bilirubin, and/or alkaline phosphatase. Elevated gamma-glutamyl transferase has been observed in some patients receiving d-pirfenidone, without clinical liver impairment, and thus elevated gamma-glutamyl transferase alone is not necessarily a sign of liver impairment. In any of the embodiments described herein, biomarkers of liver function can exclude gamma-glutamyl transferase. In another embodiment, the abnormal level of alanine transaminase, aspartate transaminase, or alkaline phosphatase is greater than about 2.5-fold increased compared to the upper limit of normal (ULN). In a related embodiment, the abnormal level of alanine transaminase, aspartate transaminase, or alkaline phosphatase is greater than about 2.5- to about 5-fold increased compared to the upper limit of normal (ULN), i.e. a "liver function Grade 2 abnormality". In some embodiments, the abnormal level of bilirubin is greater than about 1.5- to about 3-fold increased compared to the upper limit of normal (ULN), i.e., a "liver function Grade 2 abnormality".

In some embodiments the abnormal biomarkers of liver function, e.g. elevated alanine transaminase and/or aspartate transaminase and/or elevated bilirubin, are accompanied by clinical signs of impaired liver function such as jaundice.

The invention provides methods for administering a full therapeutically effective dose of d-pirfenidone to a patient that has exhibited abnormal levels of biomarkers of liver function after the patient has been treated with d-pirfenidone. Because liver function abnormalities can be indicative of drug-induced liver injury (hepatotoxicity), it is important to determine whether the abnormalities reflect liver injury or merely indicate limited toxicity that will resolve over time while continuing to take the drug. According to the present invention, even patients that exhibit abnormal liver function may continue taking d-pirfenidone at the original full target dose, optionally after a short time period of discontinuing d-pirfenidone or taking the d-pirfenidone at reduced doses. This administration regimen has the advantage of maximizing the time on the full target dose of drug and therefore the potential for a beneficial therapeutic effect. In certain embodiments, the d-pirfenidone is $d_3$-pirfenidone.

The patient may be suffering from any disease for which d-pirfenidone therapy may be useful in ameliorating symptoms. Such a patient is a patient who would benefit from d-pirfenidone administration. These diseases include, but are not limited to: chronic obstructive pulmonary disease (COPD), inflammatory pulmonary fibrosis (IPF), rheumatoid arthritis; rheumatoid spondylitis; osteoarthritis; gout, other arthritic conditions; sepsis; septic shock; endotoxic shock; gram-negative sepsis; toxic shock syndrome; myofacial pain syndrome (MPS); Shigellosis; asthma; adult respiratory distress syndrome; inflammatory bowel disease; Crohn's disease; psoriasis; eczema; ulcerative colitis; glomerular nephritis; scleroderma; chronic thyroiditis; Grave's disease; Ormond's disease; autoimmune gastritis; myasthenia gravis; autoimmune hemolytic anemia; autoimmune neutropenia; thrombocytopenia; pancreatic fibrosis; chronic active hepatitis including hepatic fibrosis; acute and chronic renal disease; renal fibrosis, irritable bowel syndrome; pyresis; restenosis; cerebral malaria; stroke and ischemic injury; neural trauma; Alzheimer's disease; Huntington's disease; Parkinson's disease; acute and chronic pain; allergies, including allergic rhinitis and allergic conjunctivitis; cardiac hypertrophy, chronic heart failure; acute coronary syndrome; cachexia; malaria; leprosy; leishmaniasis; Lyme disease; Reiter's syndrome; acute synoviitis; muscle degeneration, bursitis; tendonitis; tenosynoviitis; herniated, ruptured, or prolapsed intervertebral disk syndrome; osteopetrosis; thrombosis; silicosis; pulmonary sarcosis; bone resorption diseases, such as osteoporosis or multiple myeloma-related bone disorders; cancer, including but not limited to metastatic breast carcinoma, colorectal carcinoma, malignant melanoma, gastric cancer, and non-small cell lung cancer; graft-versus-host reaction; and auto-immune diseases, such as Multiple Sclerosis, lupus and fibromyalgia; AIDS and other viral diseases such as Herpes Zoster, Herpes Simplex I or II, influenza virus, Severe Acute Respiratory Syndrome (SARS) and cytomegalovirus; and diabetes mellitus. In addition, the methods of the embodiments can be used to treat proliferative disorders (including both benign and malignant hyperplasias), including acute myelogenous leukemia, chronic myelogenous leukemia, Kaposi's sarcoma, metastatic melanoma, multiple myeloma, breast cancer, including metastatic breast carcinoma; colorectal carcinoma; malignant melanoma; gastric cancer; non-small cell lung cancer (NSCLC); bone metastases, and the like; pain disorders including neuromuscular pain, headache, cancer pain, dental pain, and arthritis pain; angiogenic disorders including solid tumor angiogenesis, ocular neovascularization, and infantile hemangioma; conditions associated with the cyclooxygenase and lipoxygenase signaling pathways, including conditions associated with prostaglandin endoperoxide synthase-2 (including edema, fever, analgesia, and pain); organ hypoxia; thrombin-induced platelet aggregation; protozoal diseases; uterine fibroids; diabetic kidney disease; endotoxin-induced liver injury after partial hepatectomy or hepatic ischemia; allograft injury after organ transplantation; cystic fibrosis; dermatomyositis; diffuse parenchymal lung disease; mediastinal fibrosis; tuberculosis; spleen fibrosis caused by sickle-cell anemia; rheumatoid arthritis; and/or any disorder ameliorated by modulating fibrosis and/or collagen infiltration into tissues. In certain embodiments, the d-pirfenidone is $d_3$-pirfenidone.

The methods of the invention optionally include identifying abnormal liver function in a patient receiving d-pirfenidone, and monitoring biomarkers of liver function in a patient receiving a reduced dose of d-pirfenidone. In any of the methods described herein, AST and/or ALT may be elevated, e.g. to a Grade 2 or Grade 3 level. In some embodiments, the elevation is to a Grade 1 level. Alternatively, AST and bilirubin may be elevated, or AST or ALP may be elevated, or AST and GGT may be elevated, or ALT and bilirubin may be elevated, or ALT and ALP may be elevated, or ALT and GGT may be elevated, or bilirubin and ALP may be elevated, or bilirubin and GGT may be elevated, e.g., to a Grade 1, Grade 2, or Grade 3 level. Alternatively, three biomarkers of liver function may be elevated, e.g., ALT and AST and bilirubin, or ALT and AST and ALP, to a Grade 1, Grade 2, or Grade 3 level. In any of the embodiments described herein, biomarkers of liver function can exclude gamma-glutamyl transferase. In certain embodiments, the d-pirfenidone is $d_3$-pirfenidone.

In some embodiments of the methods, d-pirfenidone is administered to a patient exhibiting a liver function Grade 2 abnormality after d-pirfenidone administration as follows: (a) administering a first reduced dose of d-pirfenidone for a time period. In some embodiments, step (a) is followed by (b) administering the original full target dose. In other embodiments, the original full target dose is continued without a temporary reduction or discontinuation of the dose. In some embodiments, the time period of step (a) is 2 days, 3 days, 4 days, 5 days, 6 days, about one week, about two weeks, about three weeks, about four weeks, about 1 month, or until the level of at least one biomarker of liver function has returned to within normal limits, or until all biomarkers or liver function has returned to within normal limits. In some embodiments, step (b) is carried out for a time period of at least one week, two weeks, three weeks, four weeks or a month, two months, or three months, or one year, or two years, or three years, or four years, or five years, or seven years, or ten years, or more. Optionally the method includes measuring one or more biomarkers of liver function during step (a) and/or step (b). In certain embodiments, the d-pirfenidone is $d_3$-pirfenidone.

In some embodiments of the methods, d-pirfenidone is administered to a patient exhibiting a liver function Grade 2 abnormality as follows: (a) administering a first reduced dose of d-pirfenidone for a time period, (b) administering a second reduced dose of for a time period, and (c) administering the original full target dose. In some embodiments, the time period of step (a) is 2 days, 3 days, 4 days, 5 days, 6 days, about one week, about two weeks, about three weeks, about four weeks, about 1 month, or until the level of at least one biomarker of liver function has returned to within normal limits, or to Grade 1, or until all biomarkers or liver function has returned to within normal limits, or to Grade 1. In some embodiments, the time period of step (b) is 2 days, 3 days, 4 days, 5 days, 6 days, about one week, about two weeks, about three weeks, about four weeks, about 1 month, or until the level of at least one biomarker of liver function has returned to within normal limits, or to Grade 1, or until all biomarkers or liver function has returned to within normal limits, or to Grade 1. In some embodiments, step (c) is carried out for a time period of at least one week, two weeks, three weeks, four weeks or a month, two months, or three months, or one year, or two years, or three years, or four years, or five years, or seven years, or ten years, or more. Optionally the method includes measuring one or more biomarkers of liver function during step (a) and/or step (b) and/or step (c). In certain embodiments, the d-pirfenidone is $d_3$-pirfenidone.

In some embodiments of the methods, d-pirfenidone is administered to a patient exhibiting a liver function Grade 2 abnormality as follows: (a) discontinuing d-pirfenidone for a time period, (b) administering a first reduced dose of d-pirfenidone for a time period, (c) administering a second reduced dose of d-pirfenidone for a time period, and (d) administering the original full target dose. In some embodiments, the time period of step (a) is 2 days, 3 days, 4 days, 5 days, 6 days, about one week, about two weeks, about three weeks, about four weeks, about 1 month, or until the level of at least one biomarker of liver function has returned to within normal limits, or to Grade 1, or until all biomarkers or liver function has returned to within normal limits, or to Grade 1. In some embodiments, the time period of step (b) is 2 days, 3 days, 4 days, 5 days, 6 days, about one week, about two weeks, about three weeks, about four weeks, about 1 month, or until the level of at least one biomarker of liver function has returned to within normal limits, or to Grade 1, or until all biomarkers or liver function has returned to within normal limits, or to Grade 1. In some embodiments, the time period of step (c) is 2 days, 3 days, 4 days, 5 days, 6 days, about one week, about two weeks, about three weeks, about four weeks, about 1 month, or until the level of at least one biomarker of liver function has returned to within normal limits, or to Grade 1, or until all biomarkers or liver function has returned to within normal limits, or to Grade 1. In some embodiments, step (d) is carried out for a time period of at least one week, two weeks, three weeks, four weeks or a month, two months, or three months, or one year, or two years, or three years, or four years, or five years, or seven years, or ten years, or more. Optionally the method includes measuring one or more biomarkers of liver function during step (a) and/or step (b) and/or step (c) and/or step (d). In certain embodiments, the d-pirfenidone is $d_3$-pirfenidone.

In some embodiments of the methods, d-pirfenidone is administered to a patient exhibiting a liver function Grade 1 abnormality as follows: (a) administering a reduced dose of d-pirfenidone for a time period, and (b) administering the original full target dose. In some embodiments, the time period of step (a) is 2 days, 3 days, 4 days, 5 days, 6 days, about one week, about two weeks, about three weeks, about four weeks, about 1 month, or until the level of at least one biomarker of liver function has returned to within normal limits, or until all biomarkers or liver function has returned to within normal limits. In some embodiments, step (b) is carried out for a time period of at least one week, two weeks, three weeks, four weeks or a month, two months, or three months, or one year, or two years, or three years, or four years, or five years, or seven years, or ten years, or more. Optionally the method includes measuring one or more biomarkers of liver function during step (a) and/or step (b). In certain embodiments, the d-pirfenidone is $d_3$-pirfenidone.

In some embodiments of the methods, d-pirfenidone is administered to a patient exhibiting a liver function Grade 1 abnormality as follows: (a) administering a first reduced dose of d-pirfenidone for a time period, (b) administering a second reduced dose of d-pirfenidone for a time period, and (c) administering the original full target dose. In some embodiments, the time period of step (a) is 2 days, 3 days, 4 days, 5 days, 6 days, about one week, about two weeks, about three weeks, about four weeks, about 1 month, or until the level of at least one biomarker of liver function has returned to within normal limits, or to Grade 1, or until all biomarkers or liver function has returned to within normal limits, or to Grade 1. In some embodiments, the time period of step (b) is 2 days, 3 days, 4 days, 5 days, 6 days, about one week, about two weeks, about three weeks, about four weeks, about 1 month, or until the level of at least one biomarker of liver function has returned to within normal limits, or to Grade 1, or until all biomarkers or liver function has returned to within normal limits, or to Grade 1. In some embodiments, step (c) is carried out for a time period of at least one week, two weeks, three weeks, four weeks or a month, two months, or three months, or one year, or two years, or three years, or four years, or five years, or seven years, or ten years, or more. Optionally the method includes measuring one or more biomarkers of liver function during step (a) and/or step (b) and/or step (c). In certain embodiments, the d-pirfenidone is $d_3$-pirfenidone.

In some embodiments of the methods, d-pirfenidone is administered to a patient exhibiting a liver function Grade 1 abnormality as follows: (a) discontinuing d-pirfenidone for a time period, (b) administering a first reduced dose of d-pirfenidone for a time period, (c) administering a second reduced dose of d-pirfenidone for a time period, and (d) administering the original full target dose. In some embodiments, the time period of step (a) is 2 days, 3 days, 4 days, 5 days, 6 days, about one week, about two weeks, about three weeks, about four weeks, about 1 month, or until the level of at least one biomarker of liver function has returned to within normal limits, or to Grade 1, or until all biomarkers or liver function has returned to within normal limits, or to Grade 1. In some embodiments, the time period of step (b) is 2 days, 3 days, 4 days, 5 days, 6 days, about one week, about two weeks, about three weeks, about four weeks, about 1 month, or until the level of at least one biomarker of liver function has returned to within normal limits, or to Grade 1, or until all biomarkers or liver function has returned to within normal limits, or to Grade 1. In some embodiments, the time period of step (c) is 2 days, 3 days, 4 days, 5 days, 6 days, about one week, about two weeks, about three weeks, about four weeks, about 1 month, or until the level of at least one biomarker of liver function has returned to within normal limits, or to Grade 1, or until all biomarkers or liver function has returned to within normal limits, or to Grade 1. In some embodiments, step (d) is carried out for a time period of at least one week, two weeks, three weeks, four weeks or a month, two months, or three months, or one year, or two years, or three years, or four years, or five years, or seven years, or ten years, or more. Optionally the method includes measuring one or more biomarkers of liver function during step (a) and/or step (b) and/or step (c) and/or step (d). In certain embodiments, the d-pirfenidone is $d_3$-pirfenidone.

d-Pirfenidone can be provided in tablet or capsule forms or any other oral dosage form, and typically is formulated for oral administration. Exemplary capsule formulations are described in WO 2007/038315 (Int'l Appl. No. PCT/US2006/037057).

d-Pirfenidone therapy can be associated with adverse effects including photosensitivity rash, anorexia (decreased appetite), stomach discomfort, nausea, heartburn, drowsiness (somnolence), fatigue, upper respiratory tract infection, fever, positive urinary occult blood, elevation of C-reactive protein (CRP), decreased weight, headache, constipation, and malaise. Abnormal liver function also can occur as an adverse effect (AE) in patients receiving d-pirfenidone. Prior to receiving d-pirfenidone, the baseline liver function of the patient can be, and typically is, normal. Liver function can be assessed by various means known in the art, such as blood chemistry tests measuring biomarkers of liver function. Examples of biomarkers of liver function include, but are not limited to, alanine transaminase (ALT), aspartate transaminase (AST), bilirubin, alkaline phosphatase (ALP), and gammaglutamyl transferase (GGT).

Alanine transaminase (ALT), also called serum glutamic pyruvate transaminase (SGPT) or alanine aminotransferase (ALAT), catalyzes the transfer of an amino group from alanine to a-ketoglutarate to produce pyruvate and glutamate. When the liver is damaged, levels of ALT in the blood can rise due to the leaking of ALT into the blood from damaged or necrosed hepatocytes.

Aspartate transaminase (AST) also called serum glutamic oxaloacetic transaminase (SGOT or GOT) or aspartate aminotransferase (ASAT), catalyzes the transfer of an amino group from aspartate to a-ketoglutarate to produce oxaloacetate and glutamate. AST can increase in response to liver damage. Elevated AST also can result from damage to other sources, including red blood cells, cardiac muscle, skeletal muscle, kidney tissue, and brain tissue. The ratio of AST to ALT can be used as a biomarker of liver damage.

Bilirubin is a catabolite of heme that is cleared from the body by the liver. Conjugation of bilirubin to glucuronic acid by hepatocytes produces direct bilirubin, a water soluble product that is readily cleared from the body. Indirect bilirubin is unconjugated, and the sum of direct and indirect bilirubin constitutes total bilirubin. Elevated total bilirubin can be indicative of liver impairment.

Alkaline phosphatase (ALP) hydrolyzes phosphate groups from various molecules and is present in the cells lining the biliary ducts of the liver. ALP levels in plasma can rise in response to liver damage, and are higher in growing children and elderly patients with Paget's disease. However, elevated ALP levels usually reflect biliary tree disease.

Adverse effect Grades for abnormal liver function are defined herein by the modified Common Toxicity Criteria (CTC) provided in Table 1. See the Common Terminology Criteria for Adverse Events v3.0 (CTCAE) published Aug. 9, 2006 by the National Cancer Institute, incorporated herein by reference in its entirety.

plary values for normal ranges for a healthy adult population are set forth in Table 2 below. See Cecil Textbook of Medicine, pp. 2317-2341, W.B. Saunders & Co. (1985).

TABLE 2

| ALT | 8-20 U/L |
|---|---|
| AST | 8-20 U/L |
| Bilrubin | 0.2-1.0 mg/dL |
| | 3.4-17.1/µmol/L |
| ALP | 20-70 U/L |
| GGT | 8-40 U/L |

Grade 0 levels are characterized by biomarker levels within normal limits (WNL). "Normal" liver function, as used herein, refers to Grade 0 adverse effects. "Abnormal" liver function, as used herein, refers to Grade 1 and above adverse effects.

"Grade 1 liver function abnormalities" include elevations in ALT, AST, ALP, or GGT greater than the ULN and less than or equal to 2.5-times the ULN. Grade 1 liver function abnormalities also include elevations of bilirubin levels greater than the ULN and less than or equal to 1.5-times the ULN.

"Grade 2 liver function abnormalities" include elevations in alanine transaminase (ALT), aspartate transaminase (AST), alkaline phosphatase (ALP), or gamma-glutamyl transferase (GGT) greater than 2.5-times and less than or equal to 5-times the upper limit of normal (ULN). Grade 2 liver function abnormalities also include elevations of bilirubin levels greater than 1.5-times and less than or equal to 3-times the ULN.

"Grade 3 liver function abnormalities" include elevations in ALT, AST, ALP, or GGT greater than 5-times and less than or equal to 20-times the ULN. Grade 3 liver function abnormalities also include elevations of bilirubin levels greater than 3-times and less than or equal to 10-times the ULN.

"Grade 4 liver function abnormalities" include elevations in ALT, AST, ALP, or GGT greater than 20-times the ULN. Grade 4 liver function abnormalities also include elevations of bilirubin levels greater than 10 the ULN.

The present disclosure provides methods for treating a patient having idiopathic pulmonary fibrosis and receiving a full target dose of d-pirfenidone. In accordance with the methods, a patient with abnormal liver function is administered a second reduced dose of d-pirfenidone until liver function is within normal limits, followed by administering the patient the full target dose of d-pirfenidone per day. In certain embodiments, the d-pirfenidone is $d_3$-pirfenidone.

TABLE 1

Modified Common Toxicity Criteria

| Toxicity | Grade | | | | |
|---|---|---|---|---|---|
| | 0 | 1 | 2 | 3 | 4 |
| ALT | WNL | >ULN-2.5 × ULN | >2.5-5 × ULN | >5-20 × ULN | >20 × ULN |
| AST | WNL | >ULN-2.5 × ULN | >2.5-5 × ULN | >5-20 × ULN | >20 × ULN |
| Bilrubin | WNL | >ULN-1.5 × ULN | >1.5-3 × ULN | >3-10 × ULN | >10 × ULN |
| ALP | WNL | >ULN-2.5 × ULN | >2.5-5 × ULN | >5-20 × ULN | >20 × ULN |
| GGT | WNL | >ULN-2.5 × ULN | >2.5-5 × ULN | >5-20 × ULN | >20 × ULN |

(WNL = within normal limits; ULN = upper limit of normal)

The ULN for various indicators of liver function depends on the assay used, the patient population, and each laboratory's normal range of values for the specified biomarker, but can readily be determined by the skilled practitioner. Exem- The present disclosure also provides methods for treatment of patients that exhibit Grade 1 abnormality in one or more biomarkers of liver function after d-pirfenidone administration. In certain embodiments, the patient may be receiving d-pirfenidone for treatment of idiopathic pulmonary fibrosis.

Alternatively, the patient may be suffering from a condition for which d-pirfenidone administration may be beneficial. Optionally, patients may receive reduced doses or discontinue treatment for a time period, and then resume administration of d-pirfenidone. In certain embodiments, the d-pirfenidone is $d_3$-pirfenidone.

The present invention provides an improved dose escalation scheme for the administration of d-pirfenidone. The dose escalation scheme of the present invention provides d-pirfenidone in an amount such that the full maximum dosage is not reached for at least one week. In an embodiment, the full maximum dosage of d-pirfenidone is not reached until about Day 15 of treatment. The method of the present invention allows for a maximum dosage of d-pirfenidone per day to be administered to a patient and also reduces the incidence of adverse events associated with the administration of d-pirfenidone by more accurately matching dose escalation with tolerance development in the patient. Indeed, it has been observed that even as the dosage escalates using the dosing escalation scheme described herein, adverse events, such as somnolence, decrease. In certain embodiments, the d-pirfenidone is $d_3$-pirfenidone.

The present invention discloses a method of providing d-pirfenidone therapy to a patient comprising providing an initial daily dosage of d-pirfenidone to the patient in a first amount for the duration of a first period of time; providing a second daily dosage of d-pirfenidone to the patient in a second amount for a second period of time; and providing a final daily dosage of d-pirfenidone to the patient in a final amount for a final period of time, wherein the first and second periods of time together total at least about 7 days, or about 8, 9, 10, 11 or 12 days, or about 13 or 14 days. In some embodiments, the first and second periods can together total up to about 15 or about 20 or 21 days. In certain embodiments, the d-pirfenidone is $d_3$-pirfenidone.

In one embodiment, the first period of time is about 7 days; the second period of time is about 7 days; and the third period of time is in the range of about 1 day up to an unlimited number of days. In specific embodiments, the third period of time lasts at least about 1 month, at least about 2 months, at least about 3 months, at least about a year, at least about 18 months, at least about 2 years, or more than 2 years, at least about 3 years, at least about 4 years, at least about 5 years, or as long as therapy with d-pirfenidone is needed. In certain embodiments, the d-pirfenidone is $d_3$-pirfenidone.

The present invention also discloses a starter pack comprising dosage amounts of d-pirfenidone and compartments that separate the dosage amounts according to a daily dosage of d-pirfenidone. Advantageously, the compartments can be arranged in columns and in rows, although other arrangements are also contemplated. In certain embodiments, the d-pirfenidone is $d_3$-pirfenidone.

In one exemplary embodiment, the starter pack comprises rows designating Day numbers and separate columns for the number of times a dosage of d-pirfenidone is taken each day. In one embodiment, the starter pack may comprise separate rows for Days 1, 2, 3, 4, 5, 6, 7, 8, 9, 10, 11, 12, 13, and 14 with separate columns for dosage amounts to be taken each day. In another embodiment, each week of treatment may be designated on a separate panel. In another embodiment, each panel contained within the starter pack may be approximately the same size. In another embodiment, the starter pack has compartments arranged such that a user of the starter pack may administer the d-pirfenidone in accordance with the dose escalation method taught by the present invention. In certain embodiments, the d-pirfenidone is $d_3$-pirfenidone.

Also contemplated is use of d-pirfenidone in preparation of a medicament for the treatment of a fibrosis condition comprising administration of d-pirfenidone according to a dosing regimen as disclosed herein. In certain embodiments, the d-pirfenidone is $d_3$-pirfenidone.

The present invention discloses a method of providing d-pirfenidone therapy to a patient with an escalating dosage regimen that mitigates adverse events associated with the use of d-pirfenidone and, it is believed, better matches the development of tolerance to potentially adverse effects of the drug with increases in the dosage. In one embodiment of the present invention is a method of providing d-pirfenidone therapy to a patient comprising providing an initial daily dosage of d-pirfenidone to the patient in a first amount for the duration of a first period of time; providing a second daily dosage of d-pirfenidone to the patient in a second amount for a second period of time; and providing a final daily dosage of d-pirfenidone to the patient in a final amount for a final period of time. In certain embodiments the sum of the first and second periods of time is at least about 7 days, in further embodiments about 8, 9, 10, 11, or 12 days, and in further embodiments about 13 or 14 days. In some embodiments, the first and second periods can together total up to about 15 or about 20 or 21 days. Although it is also contemplated that the first and second periods together can total more than 21 days, and can (for example) be 22, 24, 26, or 30 days, it is believed that the longer dose escalation periods are less than optimal, due to the decrease in therapeutic benefit to the patient resulting from the delay in administering the full therapeutic dosage. In certain embodiments, the d-pirfenidone is $d_3$-pirfenidone.

Although the present disclosure exemplifies dose escalation regimens having three steps, it is also possible to have more steps in the same amount of time, so that the dosage escalates in smaller steps. Indeed, if desired, each dose can be incrementally larger than the previous dose, or the dose can escalate every day, every two days, or every three or four days, for example. Regardless of the dose escalation step size, the use of an initial dose and an ending dose in the amounts discussed below is particularly preferred.

In one embodiment, the first period of time is in the range of about 3 days to about 10 days. In another embodiment, the first period of time is about 6 to about 8 days. In another embodiment, the first period of time is about 7 days.

In one embodiment, the second period of time is in the range of about 3 days to about 10 days. In another embodiment, the second period of time is about 6 to about 8 days. In another embodiment, the second period of time is about 7 days.

In one embodiment, the final period of time is in the range of about 1 day to an unlimited number of days. In certain embodiments, the final period of time will be however long the duration of treatment with d-pirfenidone should last. In certain embodiments, the d-pirfenidone is $d_3$-pirfenidone.

In one embodiment, a dosage amount of d-pirfenidone is taken with food. In another embodiment, the patient is instructed to administer the dosage of d-pirfenidone with food. In certain embodiments, the d-pirfenidone is $d_3$-pirfenidone.

In another embodiment of the present invention, there is provided a starter pack comprising d-pirfenidone. Starter packs are a relatively easy method for singulating, transporting, storing and finally dispensing oral solid drugs. Such packs include, for instance, a planar transparent piece of plastic provided with "blisters" or convex protrusions configured in rows and columns. Each of the blisters or convex protrusions is sized to receive a singulated dosage amount of the particular oral solid drug being dispensed. In certain embodiments, the d-pirfenidone is $d_3$-pirfenidone.

Typically, at least one backing layer is fastened to a solid receiving side of the blister pack. This layer is a low strength retaining barrier. This low strength retaining layer stretches across the backs of the blisters and retains the singulated oral dosage amounts individually sealed within each of the blisters.

Dispensing of drugs from such blister packs is easy to understand. The consumer presses down on a blister from the convex side of the blister. Such pressure bears directly against the singulated oral dosage amount contained in the blister. The singulated oral solid drug is then forced through the low strength retaining barrier. This low strength retaining barrier at least partially tears and breaks away. During this partial breaking and tearing away, the singulated oral dosage amount is partially—but typically not totally—ejected from its individual blister. In certain embodiments, it is during this partial ejection that the oral solid drug is grasped by the user and consumed as directed. The result is a safe, sterile dispensing of the drug in desired single dosage amounts from the blister pack.

The starter pack of the present invention may comprise various dosage amounts of d-pirfenidone designated within blisters or other individual compartments so that the patient will take the proper dosage amount of the drug each day. The starter pack may comprise many different forms. It is contemplated that a panel may be constructed to comprise more or less compartments. For instance, a panel may be constructed to hold dosage amounts for three days of treatment. In another embodiment, a panel may be constructed to hold dosage amounts for six days of treatment. In another embodiment, a panel may be constructed to hold dosage amounts for ten days of treatment. Any number of days and dosages in a single panel are contemplated by the inventors. In certain embodiments, the starter pack may be designed so that the user administers d-pirfenidone according to the dose escalation scheme of the present invention. In certain embodiments, the d-pirfenidone is $d_3$-pirfenidone.

In one embodiment, the starter pack comprises panels giving dosage amounts of d-pirfenidone for the first week of treatment and the second week of treatment. In another embodiment, the starter pack further comprises a panel giving dosage amounts of d-pirfenidone for the third week of treatment. In another embodiment, the starter pack comprises a panel or an insert that gives instructions to a patient for administering the proper dosage amount of d-pirfenidone. In certain embodiments, the d-pirfenidone is $d_3$-pirfenidone.

In one embodiment, the starter pack may comprise only dosage amounts for the first week of treatment and the second week of treatment. In certain embodiments, such a starter pack may also comprise instructions to the patient for administering the d-pirfenidone from a bottle for therapy after dose escalation is completed. It is contemplated that the user of the starter pack will continue therapy with d-pirfenidone pills from a bottle after dose escalation is completed. In certain embodiments, the d-pirfenidone is $d_3$-pirfenidone.

The size of the starter pack and the panels that comprise the starter pack may be typical of similar starter packs already known. In a preferred embodiment, each panel within a starter pack is approximately of similar size dimensions as the other panels of the starter pack.

In some embodiments, the starter pack comprises a unitary structure, wherein the unitary structure comprises more than one panel and each panel may comprise dosage amounts for one week of treatment. In some embodiments, the starter pack comprises a panel that has printed instructions thereon. In some embodiments, the starter pack may comprise panels having compartments for containing dosages of d-pirfenidone. The dosages may be pushed through the low strength retaining barrier at points opposite the location of the blisters. In certain embodiments, the d-pirfenidone is $d_3$-pirfenidone.

The Week 1 panel may have compartments that comprise a dosage amount of d-pirfenidone related to the first week of treatment. The Week 2 panel may have compartments that comprise a dosage amount of d-pirfenidone related to the second week of treatment. Optionally, a panel for the dosage amounts of Week 3 may be included. The Week 3 panel may have compartments that comprise a dosage amount of d-pirfenidone related to the third week of usage. The other panel may be left blank or provided with instructions or any other type of indicia. In some embodiments, the starter pack may comprise an adhesive seal or a sticker that holds the starter pack in folded form until the adhesive seal or sticker is broken by a user. The starter pack may comprise regions capable of folding so that the separate panels can be stacked upon one another while the starter pack maintains its unitary structure. In certain embodiments, the d-pirfenidone is $d_3$-pirfenidone.

In one embodiment, one panel may comprise compartments giving the dosage amount for Days 1-7 of the dose escalation scheme and the second panel may comprise compartments giving the dosage amount for Days 8-14 of the dose escalation scheme. In another embodiment, an optional third panel may be further provided to comprise compartments giving the dosage amount for Days 15-21 of the dose escalation scheme.

The starter pack for the first week of treatment may comprise a panel having a plurality of compartments for containing a dosage amount of d-pirfenidone. The compartments may be arranged in column and row fashion as illustrated, although other arrangements are also contemplated, including having all of the compartments arranged in a line, or having them arranged in a circular fashion. Additionally, instructions may be provided on the starter pack indicating the proper day and time the dosage amount should be administered. In certain embodiments, the d-pirfenidone is $d_3$-pirfenidone.

The starter pack for the second week of treatment may comprise a panel having a plurality of compartments for containing a dosage amount of d-pirfenidone. The compartments for the second week of treatment may be fashioned to hold a greater amount of d-pirfenidone than the compartments for the first week of treatment. The dosage amount of d-pirfenidone for the second week may be greater than the dosage amount of the first week. Additionally, instructions may be provided on the starter pack indicating the proper day and time the dosage amount should be administered. In certain embodiments, the d-pirfenidone is $d_3$-pirfenidone.

The starter pack for the third week of treatment may comprise a panel having a plurality of compartments for containing a dosage amount of d-pirfenidone. The compartments for the third week of treatment may be fashioned to hold a greater amount of d-pirfenidone than the compartments for the second week of treatment. The dosage amount of d-pirfenidone for the third week may be greater than the dosage amount of the second week. Additionally, instructions may be provided on the starter pack indicating the proper day and time the dosage amount should be administered. In certain embodiments, the d-pirfenidone is $d_3$-pirfenidone.

In some embodiments, the starter pack may comprise a casing material that holds separate panels, wherein at least one panel comprises a plurality of compartments for containing a dosage amount of d-pirfenidone. In some embodiments, the panel may be located within a container having flat outer surfaces so that the container may easily be slid in and out of the casing material. In one embodiment, each container may comprise a panel that comprises a plurality of compartments that hold a dosage amount of d-pirfenidone. In some embodiments, the panels may further comprise instructions or indicia so that a user can administer d-pirfenidone according to the dose escalation scheme. In some embodiments, a panel may be provided separately for providing indicia or instructions on using the drug. In some embodiments, indicia or instructions may be provided on one or more of the containers. In certain embodiments, the d-pirfenidone is $d_3$-pirfenidone.

In certain embodiments a starter pack comprises a casing material and at least one container. The container is partially pulled out from the casing material and may comprise a panel having a plurality of compartments for containing a dosage amount of d-pirfenidone. In certain embodiments, each panel will be approximately the same size for easy and compact insertion into the casing material. In certain embodiments, the d-pirfenidone is $d_3$-pirfenidone.

One embodiment of the present invention is a starter pack comprising dosage amounts of d-pirfenidone and compartments that separate the dosage amounts according to a daily dosage of d-pirfenidone. In one embodiment, the starter pack comprises a row designating Day numbers and separate columns for the number of times a dosage of d-pirfenidone is taken each day. In one embodiment, the starter pack may comprise separate rows for Days 1, 2, 3, 4, 5, 6, 7, 8, 9, 10, 11, 12, 13, and 14 with separate columns for dosage amounts to be taken each day. In another embodiment, each panel contained within the starter pack may be approximately the same size. In another embodiment, the starter pack has compartments arranged such that a user of the starter pack will administer the d-pirfenidone in accordance with the dose escalation method taught by the present invention. In certain embodiments, the d-pirfenidone is $d_3$-pirfenidone.

In one embodiment, the starter pack further comprises additional rows for Days 15, 16, 17, 18, 19, 20, and 21. In another embodiment, each of the compartments corresponding to Days 15, 16, 17, 18, 19, 20, and 21 separately contain a dosage of d-pirfenidone. The addition of the rows for Days 15, 16, 17, 18, 19, 20, and 21 is for the purpose of training the patient as to the correct amount of dosage that will be needed after the starter pack is finished and the patient begins taking pills from another source, such as a pill bottle. By providing the starter pack with a third week at the full dosage of d-pirfenidone, the patient will be better accustomed to taking the dosage from Day 15 and each Day thereafter as required by the d-pirfenidone therapy method of the present invention. In certain embodiments, the d-pirfenidone is $d_3$-pirfenidone.

In another embodiment, the starter pack comprises a circular form. In certain embodiments a container comprises a base that holds at least one panel having a plurality of compartments for containing a dosage amount of d-pirfenidone. The panel is circular in shape with compartments extending in a radial pattern from the center and wherein each radius designates its own Day for treatment with d-pirfenidone. The dosages for AM, noon, and PM may be separated. The container also comprises a lid so that at least one panel containing d-pirfenidone can be stored within the container and sealed. In certain embodiments, the d-pirfenidone is $d_3$-pirfenidone.

In certain embodiments a starter pack comprises dosage amounts for the first week of therapy using d-pirfenidone. The starter pack for the first week of treatment may comprise a circular panel having a plurality of compartments for containing a dosage amount of d-pirfenidone. The compartments may be arranged so that they extend radially from the center of the pane. The panel may comprise indicia informing the patient which dosage to administer at the appropriate time. In certain embodiments, the d-pirfenidone is $d_3$-pirfenidone.

In certain embodiments a starter pack comprises dosage amounts for the second week of therapy using d-pirfenidone. The starter pack for the second week of treatment may comprise a circular panel having a plurality of compartments for containing a dosage amount of d-pirfenidone. The compartments may be arranged so that they extend radially from the center or so that they fit within a panel. The panel may comprise indicia informing the patient which dosage to administer at the appropriate time. In certain embodiments, the d-pirfenidone is $d_3$-pirfenidone.

In certain embodiments a starter pack comprises dosage amounts for the third week of therapy using d-pirfenidone. The panel for the third week of therapy is optionally provided. The starter pack for the third week of treatment may comprise a circular panel having a plurality of compartments for containing a dosage amount of d-pirfenidone. The compartments may be arranged so that they extend radially from the center of the pane. The panel may comprise indicia informing the patient which dosage to administer at the appropriate time. In certain embodiments, the d-pirfenidone is $d_3$-pirfenidone.

In another embodiment, the starter pack has compartments arranged such that a user of the starter pack will administer the d-pirfenidone in accordance with the dose escalation method taught by the present invention. Of course, as an alternative to blister packs, the doses can be contained in any other type of compartment, such as plastic bags or other containers fastened together in book form; plastic containers with snap-open lids arranged in a row or other geometric pattern, or any of a wide variety of other dosage-containing packages. In certain embodiments, the d-pirfenidone is $d_3$-pirfenidone.

In one embodiment, a method for administering d-pirfenidone therapy to a patient comprises initially administering a predetermined starting dosage of d-pirfenidone to the patient and escalating the dosage administered to the patient over a predetermined time to a predetermined full dosage of d-pirfenidone. In some embodiments, the predetermined time is measured from the initial starting dosage and is between about 7 and 20 days. In some embodiments, the predetermined time is 13 or 14 days. In some embodiments, the dosages are split into one, two, or three daily oral administrations. In certain embodiments, the d-pirfenidone is $d_3$-pirfenidone.

INCORPORATION BY REFERENCE

All publications and references cited herein, including those in the background section, are expressly incorporated herein by reference in their entirety. However, with respect to any similar or identical terms found in both the incorporated publications or references and those expressly put forth or defined in this document, then those terms definitions or meanings expressly put forth in this document shall control in all respects.

DETAILED DESCRIPTION

To facilitate understanding of the disclosure set forth herein, a number of terms are defined below. Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood in the art to which this disclosure belongs. In the event that there is a plurality of definitions for a term used herein, those in this section prevail unless stated otherwise.

As used herein, the singular forms "a," "an," and "the" may refer to plural articles unless specifically stated otherwise.

The term "d-pirfenidone" refers to a compound of structural Formula I:

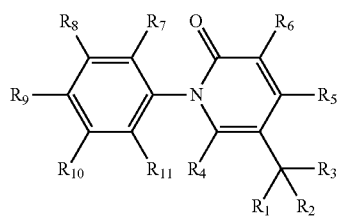

or a pharmaceutically acceptable salt, solvate, or prodrug thereof; wherein:

$R_1$, $R_2$, $R_3$, $R_4$, $R_5$, $R_6$, $R_7$, $R_8$, $R_9$, $R_{10}$, and $R_{11}$ are selected from the group consisting of hydrogen or deuterium; and at least one $R_1$, $R_2$, $R_3$, $R_4$, $R_5$, $R_6$, $R_7$, $R_8$, $R_9$, $R_{10}$, and $R_{11}$ is deuterium. In certain embodiments, the d-pirfenidone is $d_3$-pirfenidone having the following structural formula:

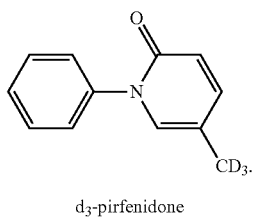

$d_3$-pirfenidone

The term "subject" refers to an animal, including, but not limited to, a primate (e.g., human monkey, chimpanzee, gorilla, and the like), rodents (e.g., rats, mice, gerbils, hamsters, ferrets, and the like), lagomorphs, swine (e.g., pig, miniature pig), equine, canine, feline, and the like. The terms "subject" and "patient" are used interchangeably herein in reference, for example, to a mammalian subject, such as a human patient.

The terms "treat," "treating," and "treatment" are meant to include alleviating or abrogating a disorder; or alleviating or abrogating one or more of the symptoms associated with the disorder; and/or alleviating or eradicating the cause(s) of the disorder itself.

The terms "prevent," "preventing," and "prevention" refer to a method of delaying or precluding the onset of a disorder; delaying or precluding its attendant symptoms; barring a subject from acquiring a disorder; and/or reducing a subject's risk of acquiring a disorder.

The term "therapeutically effective amount" refers to the amount of a compound that, when administered, is sufficient to prevent development of, or alleviate to some extent, one or more of the symptoms of the disorder being treated. The term "therapeutically effective amount" also refers to the amount of a compound that is sufficient to elicit the biological or medical response of a cell, tissue, system, animal, or human that is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. Each component must be "pharmaceutically acceptable" in the sense of being compatible with the other ingredients of a pharmaceutical formulation. It must also be suitable for use in contact with the tissue or organ of humans and animals without excessive toxicity, irritation, allergic response, immunogenecity, or other problems or complications, commensurate with a reasonable benefit/risk ratio. See, *Remington: The Science and Practice of Pharmacy,* 21st Edition; Lippincott Williams & Wilkins: Philadelphia, Pa., 2005; Handbook of Pharmaceutical Excipients, 5th Edition; Rowe et al., Eds., The Pharmaceutical Press and the American Pharmaceutical Association: 2005; and *Handbook of Pharmaceutical Additives,* 3rd Edition; Ash and Ash Eds., Gower Publishing Company: 2007; *Pharmaceutical Preformulation and Formulation,* Gibson Ed., CRC Press LLC: Boca Raton, Fla., 2004).

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods, such as mass spectrometry and nuclear magnetic resonance spectroscopy.

The term "is/are deuterium," when used to describe a given position in a molecule such as $R_1$, $R_2$, $R_3$, $R_4$, $R_5$, $R_6$, $R_7$, $R_8$, $R_9$, $R_{10}$, and $R_{11}$ or the symbol "D," when used to represent a given position in a drawing of a molecular structure, means that the specified position is enriched with deuterium above the naturally occurring distribution of deuterium. In an embodiment deuterium enrichment is of no less than about 1%, in another no less than about 5%, in another no less than about 10%, in another no less than about 20%, in another no less than about 50%, in another no less than about 70%, in another no less than about 80%, in another no less than about 90%, or in another no less than about 98% of deuterium at the specified position.

The term "isotopic enrichment" refers to the percentage of incorporation of a less prevalent isotope of an element at a given position in a molecule in the place of the more prevalent isotope of the element.

The term "non-isotopically enriched" refers to a molecule in which the percentages of the various isotopes are substantially the same as the naturally occurring percentages.

The terms "substantially pure" and "substantially homogeneous" mean sufficiently homogeneous to appear free of readily detectable impurities as determined by standard analytical methods, including, but not limited to, thin layer chromatography (TLC), gel electrophoresis, high performance liquid chromatography (HPLC), nuclear magnetic resonance (NMR), and mass spectrometry (MS); or sufficiently pure such that further purification would not detectably alter the physical and chemical properties, or biological and pharmacological properties, such as enzymatic and biological activities, of the substance. In certain embodiments, "substantially pure" or "substantially homogeneous" refers to a collection of molecules, wherein at least about 50%, at least about 70%, at least about 80%, at least about 90%, at least about 95%, at least about 98%, at least about 99%, or at least about 99.5% of the molecules are a single compound, including a racemic mixture or single stereoisomer thereof, as determined by standard analytical methods.

The term "about" or "approximately" means an acceptable error for a particular value, which depends in part on how the value is measured or determined. In certain embodiments, "about" can mean 1 or more standard deviations.

The terms "active ingredient" and "active substance" refer to a compound, which is administered, alone or in combination with one or more pharmaceutically acceptable excipients and/or carriers, to a subject for treating, preventing, or ameliorating one or more symptoms of a disorder.

The terms "drug," "therapeutic agent," and "chemotherapeutic agent" refer to a compound, or a pharmaceutical composition thereof, which is administered to a subject for treating, preventing, or ameliorating one or more symptoms of a disorder.

The term "disorder" as used herein is intended to be generally synonymous, and is used interchangeably with, the terms "disease," "sydrome" and "condition" (as in medical condition), in that all reflect an abnormal condition of the body or of one of its parts that impairs normal functioning and is typically manifested by distinguishing signs and symptoms.

The term "release controlling excipient" refers to an excipient whose primary function is to modify the duration or place of release of the active substance from a dosage form as compared with a conventional immediate release dosage form.

The term "nonrelease controlling excipient" refers to an excipient whose primary function do not include modifying the duration or place of release of the active substance from a dosage form as compared with a conventional immediate release dosage form.

The term "protecting group" or "removable protecting group" refers to a group which, when bound to a functionality, such as the oxygen atom of a hydroxyl or carboxyl group, or the nitrogen atom of an amino group, prevents reactions from occurring at that functional group, and which can be removed by a conventional chemical or enzymatic step to reestablish the functional group (Greene and Wuts, Protective Groups in Organic Synthesis, $3^{rd}$ Ed., John Wiley & Sons, New York, N.Y., 1999).

The term "fibrosis" refers to the development of excessive fibrous connective tissue within an organ or tissue.

The term "collagen infiltration" refers to the entry of the connective tissue collagen into cells or into the extracellular matrix around cells. This occurs in organs and tissues naturally and under normal circumstances but can occur excessively and accompany or cause disease.

The terms "fibrosis" and "collagen infiltration" are not necessarily synonymous but can, in certain contexts, be used interchangeably.

As used herein, the terms "adverse event" and "adverse reactions" refer to any unfavorable, harmful, or pathologic change in a patient receiving pirfenidone therapy as indicated by physical signs, symptoms, and/or clinically significant laboratory abnormalities that occur in a patient during the treatment and post-treatment period, regardless of suspected cause. This definition includes the following: intercurrent illness; injuries; exacerbation of pre-existing conditions; adverse events occurring as a result of product withdrawal, abuse, or overdose; and a change in a laboratory variable if considered by the attending physician to be clinically significant or if it caused (or should have caused) the clinician to reduce or discontinue the use of the product or initiate a nonprotocol therapy or procedure.

As used herein, the term "with food" is defined to mean, in general, the condition of having consumed food during the period between from about 1 hour prior to the administration of pirfenidone to about 2 hours after the administration of pirfenidone.

The terms "without food," "fasted," or "on an empty stomach" are defined to mean the condition of not having consumed food within the time period of about 1 hour prior to the administration of pirfenidone to about 2 hours after the administration of pirfenidone. In some embodiments, food has not been consumed for about 10 hours, about 8 hours, about 6 hours, about 4 hours, about 2 hours prior to administration of pirfenidone.

The term "at risk for or suffering from" as used herein, refers to subjects having previously experienced, or currently experiencing, or having a high probability of experiencing an adverse event associated with pirfenidone therapy. Methods for identifying a subject at risk for or suffering from such adverse events are known in the art.

Deuterated Pyridinone Derivatives

Pirfenidone is a substituted pyridinone-based fibrosis modulator and/or collagen infiltration modulator. The carbon-hydrogen bonds of pirfenidone contain a naturally occurring distribution of hydrogen isotopes, namely $^1$H or protium (about 99.9844%), $^2$H or deuterium (about 0.0156%), and $^3$H or tritium (in the range between about 0.5 and 67 tritium atoms per $10^{18}$ protium atoms). Increased levels of deuterium incorporation may produce a detectable Kinetic Isotope Effect (KIE) that could affect the pharmacokinetic, pharmacologic and/or toxicologic profiles of such fibrosis modulators and/or collagen-infiltration modulators in comparison with the compound having naturally occurring levels of deuterium.

Pirfenidone is likely metabolized in humans by oxidizing the methyl group. Other sites on the molecule may also undergo transformations leading to metabolites with as-yet-unknown pharmacology/toxicology. Limiting the production of these metabolites has the potential to decrease the danger of the administration of such drugs and may even allow increased dosage and concomitant increased efficacy. All of these transformations can occur through polymorphically-expressed enzymes, thus exacerbating the interpatient variability. Further, disorders, such as multiple sclerosis, are best treated when the subject is medicated around the clock for an extended period of time. For all of foregoing reasons, there is a strong likelihood that a longer half-life medicine will diminish these problems with greater efficacy and cost savings.

Various deuteration patterns can be used to a) reduce or eliminate unwanted metabolites, b) increase the half-life of the parent drug, c) decrease the number of doses needed to achieve a desired effect, d) decrease the amount of a dose needed to achieve a desired effect, e) increase the formation of active metabolites, if any are formed, and/or f) decrease the production of deleterious metabolites in specific tissues and/or create a more effective drug and/or a safer drug for polypharmacy, whether the polypharmacy be intentional or not. The deuteration approach has strong potential to slow the metabolism via various oxidative and racemization mechanisms.

In one aspect, disclosed herein is a compound having structural Formula I:

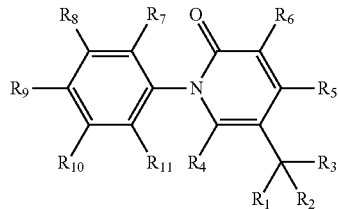

or a pharmaceutically acceptable salt, solvate, or prodrug thereof; wherein:

$R_1$, $R_2$, $R_3$, $R_4$, $R_5$, $R_6$, $R_7$, $R_8$, $R_9$, $R_{10}$, and $R_{11}$ are selected from the group consisting of hydrogen and deuterium; and at least one of $R_1$, $R_2$, $R_3$, $R_4$, $R_5$, $R_6$, $R_7$, $R_8$, $R_9$, $R_{10}$, and $R_{11}$ is deuterium; and when $R_7$, $R_8$, $R_9$, $R_{10}$, and $R_{11}$ are deuterium, then at least one of $R_1$, $R_2$, $R_3$, $R_4$, $R_5$, and $R_6$ is deuterium.

In another embodiment, at least one of $R_1$, $R_2$, $R_3$, $R_4$, $R_5$, $R_6$, $R_7$, $R_8$, $R_9$, $R_{10}$, and $R_{11}$ independently has deuterium enrichment of no less than about 1%, no less than about 5%, no less than about 10%, no less than about 20%, no less than about 50%, no less than about 70%, no less than about 80%, no less than about 90%, or no less than about 98%.

In yet another embodiment, at least one of $R_1$, $R_2$, and $R_3$ is deuterium.

In yet another embodiment, $R_1$, $R_2$, and $R_3$ are deuterium.

In yet another embodiment, $R_4$ is deuterium.

In yet another embodiment, at least one of $R_5$ and $R_6$ is deuterium.

In yet another embodiment, $R_5$ and $R_6$ are deuterium.

In yet another embodiment, $R_5$ and $R_6$ are deuterium; and at least one of $R_1$, $R_2$, $R_3$, $R_4$, $R_7$, $R_8$, $R_9$, $R_{10}$, and $R_{11}$ is deuterium.

In yet another embodiment, at least one of $R_7$, $R_8$, $R_9$, $R_{10}$, and $R_{11}$ is deuterium.

In yet another embodiment, $R_7$, $R_8$, $R_9$, $R_{10}$, and $R_{11}$ are deuterium.

In yet another embodiment, $R_7$, $R_8$, and $R_9$ are deuterium, and at least one of $R_1$, $R_2$, $R_3$, $R_4$, $R_5$, $R_6$, $R_{10}$, and $R_{11}$ is deuterium.

In yet another embodiment, at least one of $R_1$, $R_2$, and $R_3$ is deuterium; and $R_4$, $R_5$, $R_6$, $R_7$, $R_8$, $R_9$, $R_{10}$, and $R_{11}$ are hydrogen.

In yet another embodiment, $R_1$, $R_2$, and $R_3$ are deuterium; and $R_4$, $R_5$, $R_6$, $R_7$, $R_8$, $R_9$, $R_{10}$, and $R_{11}$ are hydrogen.

In yet another embodiment, $R_4$ is deuterium; and $R_1$, $R_2$, $R_3$, $R_5$, $R_6$, $R_7$, $R_8$, $R_9$, $R_{10}$, and $R_{11}$ are hydrogen.

In yet another embodiment, at least one of $R_5$ and $R_6$ is deuterium; and $R_1$, $R_2$, $R_3$, $R_4$, $R_7$, $R_8$, $R_9$, $R_{10}$, and $R_{11}$ are hydrogen.

In yet another embodiment, $R_5$ and $R_6$ are deuterium; and $R_1$, $R_2$, $R_3$, $R_4$, $R_7$, $R_8$, $R_9$, $R_{10}$, and $R_{11}$ are hydrogen.

In yet another embodiment, at least one of $R_1$, $R_2$, $R_3$, $R_4$, $R_5$ and $R_6$ is deuterium; and $R_7$, $R_8$, $R_9$, $R_{10}$, and $R_{11}$ are hydrogen.

In yet another embodiment, $R_1$, $R_2$, $R_3$, $R_4$, $R_5$ and $R_6$ are deuterium; and $R_7$, $R_8$, $R_9$, $R_{10}$, and $R_{11}$ are hydrogen.

In yet another embodiment, at least one of $R_7$, $R_8$, $R_9$, $R_{10}$, and $R_{11}$ is deuterium; and $R_1$, $R_2$, $R_3$, $R_4$, $R_5$, and $R_6$ are hydrogen.

In yet another embodiment, $R_7$, $R_8$, $R_9$, $R_{10}$, and $R_{11}$ are deuterium; and at least one of $R_1$, $R_2$, $R_3$, $R_4$, $R_5$, and $R_6$ is deuterium.

In other embodiments, $R_1$ is hydrogen. In yet other embodiments, $R_2$ is hydrogen. In still other embodiments, $R_3$ is hydrogen. In yet other embodiments, $R_4$ is hydrogen. In some embodiments, $R_5$ is hydrogen. In yet other embodiments, $R_6$ is hydrogen. In still other embodiments, $R_7$ is hydrogen. In still other embodiments, $R_8$ is hydrogen. In some embodiments, $R_9$ is hydrogen. In other embodiments, $R_{10}$ is hydrogen. In yet other embodiments, $R_{11}$ is hydrogen.

In other embodiments, $R_1$ is deuterium. In yet other embodiments, $R_2$ is deuterium. In still other embodiments, $R_3$ is deuterium. In yet other embodiments, $R_4$ is deuterium. In some embodiments, $R_5$ is deuterium. In yet other embodiments, $R_6$ is deuterium. In still other embodiments, $R_7$ is deuterium. In still other embodiments, $R_8$ is deuterium. In some embodiments, $R_9$ is deuterium. In other embodiments, $R_{10}$ is deuterium. In yet other embodiments, $R_{11}$ is deuterium.

In yet another embodiment, the compound of Formula I is selected from the group consisting of:

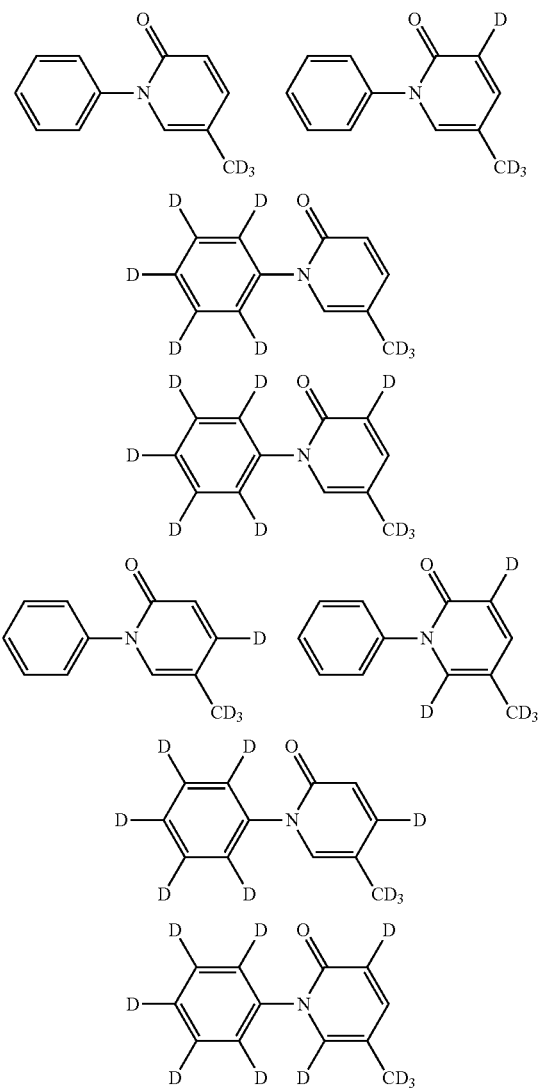

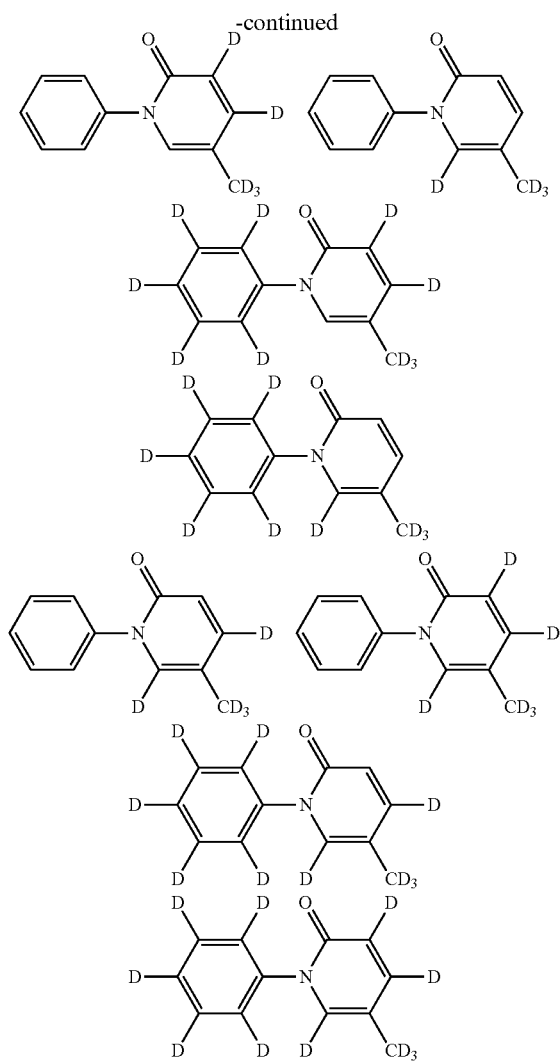

or a pharmaceutically acceptable salt, solvate, or prodrug thereof.

In another embodiment, at least one of the positions represented as D independently has deuterium enrichment of no less than about 1%, no less than about 5%, no less than about 10%, no less than about 20%, no less than about 50%, no less than about 70%, no less than about 80%, no less than about 90%, or no less than about 98%.

The deuterated compound as disclosed herein may also contain less prevalent isotopes for other elements, including, but not limited to, $^{13}C$ or $^{14}C$ for carbon, $^{15}N$ for nitrogen, and $^{17}O$ or $^{18}O$ for oxygen.

In one embodiment, the deuterated compounds disclosed herein maintain the beneficial aspects of the corresponding non-isotopically enriched molecules while substantially increasing the maximum tolerated dose, decreasing toxicity, increasing the half-life ($T_{1/2}$), lowering the maximum plasma concentration ($C_{max}$) of the minimum efficacious dose (MED), lowering the efficacious dose and thus decreasing the non-mechanism-related toxicity, and/or lowering the probability of drug-drug interactions.

Isotopic hydrogen can be introduced into a compound of a compound disclosed herein as disclosed herein by synthetic techniques that employ deuterated reagents, whereby incorporation rates are pre-determined; and/or by exchange techniques, wherein incorporation rates are determined by equilibrium conditions, and may be highly variable depending on the reaction conditions. Synthetic techniques, where tritium or deuterium is directly and specifically inserted by tritiated or deuterated reagents of known isotopic content, may yield high tritium or deuterium abundance, but can be limited by the chemistry required. In addition, the molecule being labeled may be changed, depending upon the severity of the synthetic reaction employed. Exchange techniques, on the other hand, may yield lower tritium or deuterium incorporation, often with the isotope being distributed over many sites on the molecule, but offer the advantage that they do not require separate synthetic steps and are less likely to disrupt the structure of the molecule being labeled.

The compounds as disclosed herein can be prepared by methods known to one of skill in the art and routine modifications thereof, and/or following procedures similar to those described in the Example section herein and routine modifications thereof, and/or procedures found in Esaki et al *Tetrahedron* 2006, 62, 10954-10961, Smith et al *Organic Syntheses* 2002, 78, 51-56, U.S. Pat. No. 3,974,281 and WO2003/014087, and references cited therein and routine modifications thereof. Compounds as disclosed herein can also be prepared as shown in any of the following schemes and routine modifications thereof.

For example, certain compounds as disclosed herein can be prepared as shown in Schemes 1 and 2.

Scheme 1

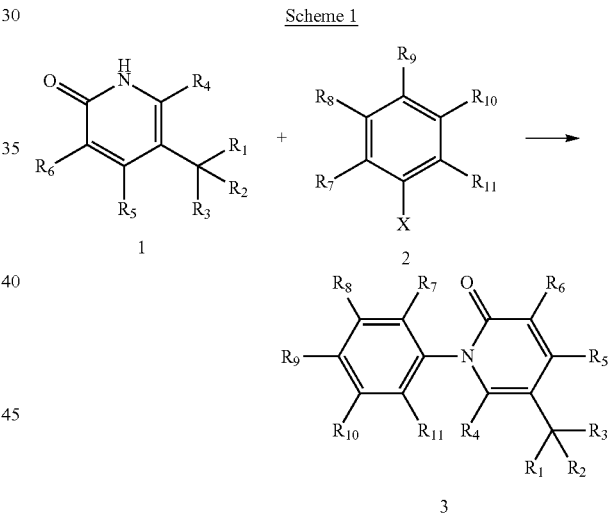

Aminopyridone 1 when treated with a base, such as potassium carbonate, and in the presence of a copper containing reagent, such as copper powder, reacts with benzene 2 (wherein X is either Bromine or Iodine) at an elevated temperature with or without solvent to afford N-aryl pyridinone 3 of Formula 1.

Deuterium is incorporated into different positions synthetically, according to the synthetic procedures as shown in Scheme 1, by using appropriate deuterated intermediates. For example, to introduce deuterium at positions $R_1$, $R_2$, $R_3$, $R_4$, $R_5$, and $R_6$, 2-hydroxy-5-picoline with the corresponding deuterium substitutions can be used. To introduce deuterium at one or more positions selected from $R_7$, $R_8$, $R_9$, $R_{10}$ and $R_{11}$, the appropriate halobenzene with the corresponding deuterium substitutions can be used. These deuterated intermediates are either commercially available, or are prepared by methods known to one of skill in the art or following procedures similar to those described in the Example section herein and routine modifications thereof.

Deuterium can also be incorporated to various positions having an exchangeable proton via proton-deuterium equilibrium exchange. Such protons may be replaced with deuterium selectively or non-selectively through a proton-deuterium exchange method known in the art.

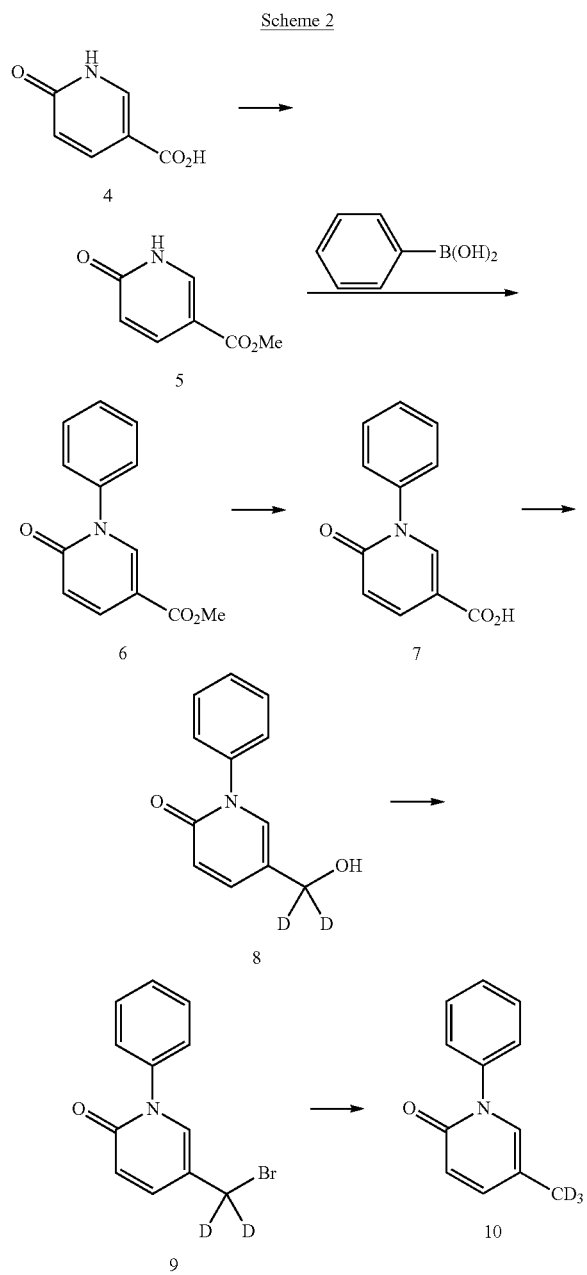

6-Hydroxynicotinic acid (4) reacts with thionyl chloride and methanol to give methyl-6-oxo-1,6-dihydropyridine-3-carboxylate (5), which is coupled with phenylboronic acid in the presence of copper(II) acetate monohydrate, pyridine and molecular sieves in dichloromethane to give methyl-6-oxo-1-phenyl-1,6-dihydropyridine-3-carboxylate (6). Compound 6 is hydrolyzed with lithium hydroxide monohydrate in tetrahydrofuran water, to give 6-oxo-1-phenyl-1,6-dihydropyridine-3-carboxylic acid 7. Acid 7 reacts with isobutyl chloroformate in the presence of N-methylmorpholine in tetrahydrofuran to give a mixed anhydride which is reduced with sodium borodeuteride in tetrahydrofuran to give $d_2$-5-(hydroxymethyl)-1-phenylpyridine-2(1H)-one (8). Compound 8 is converted to $d_2$-5-bromomethyl-1-phenyl-1H-pyridin-2-one (9) by reacting with phosphorus tribromide in dichloromethane. Bromide 9 is reduced with lithium aluminum deuteride to give $d_3$-5-(methyl)-1-phenylpyridine-2 (1H)-one (10) of Formula (I).

It is to be understood that the compounds disclosed herein may contain one or more chiral centers, chiral axes, and/or chiral planes, as described in "Stereochemistry of Carbon Compounds" Eliel and Wilen, John Wiley & Sons, New York, 1994, pp. 1119-1190. Such chiral centers, chiral axes, and chiral planes may be of either the (R) or (S) configuration, or may be a mixture thereof.

Another method for characterizing a composition containing a compound having at least one chiral center is by the effect of the composition on a beam of polarized light. When a beam of plane polarized light is passed through a solution of a chiral compound, the plane of polarization of the light that emerges is rotated relative to the original plane. This phenomenon is known as optical activity, and compounds that rotate the plane of polarized light are said to be optically active. One enantiomer of a compound will rotate the beam of polarized light in one direction, and the other enantiomer will rotate the beam of light in the opposite direction. The enantiomer that rotates the polarized light in the clockwise direction is the (+) enantiomer, and the enantiomer that rotates the polarized light in the counterclockwise direction is the (−) enantiomer. Included within the scope of the compositions described herein are compositions containing between 0 and 100% of the (+) and/or (−) enantiomer of compounds disclosed herein.

Where a compound as disclosed herein contains an alkenyl or alkenylene group, the compound may exist as one or mixture of geometric cis/trans (or Z/E) isomers. Where structural isomers are interconvertible via a low energy barrier, the compound disclosed herein may exist as a single tautomer or a mixture of tautomers. This can take the form of proton tautomerism in the compound disclosed herein that contains for example, an imino, keto, or oxime group; or so-called valence tautomerism in the compound that contain an aromatic moiety. It follows that a single compound may exhibit more than one type of isomerism.

The compounds disclosed herein may be enantiomerically pure, such as a single enantiomer or a single diastereomer, or be stereoisomeric mixtures, such as a mixture of enantiomers, a racemic mixture, or a diastereomeric mixture. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include chiral synthesis from a suitable optically pure precursor or resolution of the racemate using, for example, chiral chromatography, recrystallization, resolution, diastereomeric salt formation, or derivatization into diastereomeric adducts followed by separation.

When the compound disclosed herein contains an acidic or basic moiety, it may also disclosed as a pharmaceutically acceptable salt (See, Berge et al., *J. Pharm. Sci.* 1977, 66, 1-19; and "Handbook of Pharmaceutical Salts, Properties, and Use," Stah and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound as disclosed herein may also be designed as a prodrug, which is a functional derivative of the compound as disclosed herein and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs*, 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al., *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; Waller et al., *Br. J. Clin. Pharmac.* 1989, 28, 497-507.

Pharmaceutical Composition

Disclosed herein are pharmaceutical compositions comprising a compound as disclosed herein, or a pharmaceutically acceptable salt, solvate, or prodrug thereof, as an active ingredient, combined with a pharmaceutically acceptable vehicle, carrier, diluent, or excipient, or a mixture thereof; in combination with one or more pharmaceutically acceptable excipients or carriers.

Disclosed herein are pharmaceutical compositions in modified release dosage forms, which comprise a compound as disclosed herein, or a pharmaceutically acceptable salt, solvate, or prodrug thereof; and one or more release controlling excipients or carriers as described herein. Suitable modified release dosage vehicles include, but are not limited to, hydrophilic or hydrophobic matrix devices, water-soluble separating layer coatings, enteric coatings, osmotic devices, multiparticulate devices, and combinations thereof. The pharmaceutical compositions may also comprise non-release controlling excipients or carriers.

Further disclosed herein are pharmaceutical compositions in enteric coated dosage forms, which comprise a compound as disclosed herein, or a pharmaceutically acceptable salt, solvate, or prodrug thereof; and one or more release controlling excipients or carriers for use in an enteric coated dosage form. The pharmaceutical compositions may also comprise non-release controlling excipients or carriers.

Further disclosed herein are pharmaceutical compositions in effervescent dosage forms, which comprise a compound as disclosed herein, or a pharmaceutically acceptable salt, solvate, or prodrug thereof; and one or more release controlling excipients or carriers for use in an effervescent dosage form. The pharmaceutical compositions may also comprise non-release controlling excipients or carriers.

Additionally disclosed are pharmaceutical compositions in a dosage form that has an instant releasing component and at least one delayed releasing component, and is capable of giving a discontinuous release of the compound in the form of at least two consecutive pulses separated in time from 0.1 up to 24 hours. The pharmaceutical compositions comprise a compound as disclosed herein, or a pharmaceutically acceptable salt, solvate, or prodrug thereof; and one or more release controlling and non-release controlling excipients or carriers, such as those excipients or carriers suitable for a disruptable semi-permeable membrane and as swellable substances.

Disclosed herein also are pharmaceutical compositions in a dosage form for oral administration to a subject, which comprise a compound as disclosed herein, or a pharmaceutically acceptable salt, solvate, or prodrug thereof; and one or more pharmaceutically acceptable excipients or carriers, enclosed in an intermediate reactive layer comprising a gastric juice-resistant polymeric layered material partially neutralized with alkali and having cation exchange capacity and a gastric juice-resistant outer layer.

Disclosed herein are pharmaceutical compositions that comprise about 0.1 to about 1000 mg, about 1 to about 500 mg, about 2 to about 100 mg, about 1 mg, about 10 mg, about 25 mg, about 50 mg, about 75 mg, about 100 mg, about 150 mg, about 200 mg, about 250 mg, about 300 mg, about 350 mg, about 400 mg, about 450 mg, about 500 mg of one or more compounds as disclosed herein in the form of film-coated immediate-release tablets for oral administration. The pharmaceutical compositions further comprise hypromellose, hydroxypropyl cellulose, croscarmellose sodium, magnesium stearate, microcrystalline cellulose, povidone, pregelatinized starch, propylene glycol, silicon dioxide, sorbic acid, sorbitan monooleate, stearic acid, talc, titanium dioxide, and vanillin.

Provided herein are pharmaceutical compositions that comprise about 0.1 to about 1000 mg, about 1 to about 500 mg, about 2 to about 250 mg, about 1 mg, about 10 mg, about 25 mg, about 50 mg, about 75 mg, about 100 mg, about 150 mg, about 200 mg, about 250 mg, about 300 mg, about 350 mg, about 400 mg, about 450 mg, about 500 mg of one or more compounds as disclosed herein in the form of film-coated immediate-release tablets for oral administration. The pharmaceutical compositions further comprise hypromellose, hydroxypropyl cellulose, colloidal silicon dioxide, croscarmellose sodium, magnesium stearate, microcrystalline cellulose, povidone, propylene glycol, sorbic acid, sorbitan monooleate, titanium dioxide, and vanillin.

Provided herein are pharmaceutical compositions that comprise about 0.1 to about 1000 mg, about 1 to about 500 mg, about 2 to about 250 mg, about 1 mg, about 10 mg, about 25 mg, about 50 mg, about 75 mg, about 100 mg, about 150 mg, about 200 mg, about 250 mg, about 300 mg, about 350 mg, about 400 mg, about 450 mg, about 500 mg of one or more compounds as disclosed herein in the form of film-coated extended-release tablets for oral administration. The pharmaceutical compositions further comprise cellulosic polymers, lactose monohydrate, magnesium stearate, propylene glycol, sorbic acid, sorbitan monooleate, talc, titanium dioxide, and vanillin.

Provided herein are pharmaceutical compositions that comprise about 0.1 to about 1000 mg, about 1 to about 500 mg, about 2 to about 250 mg, about 1 mg, about 10 mg, about 25 mg, about 50 mg, about 75 mg, about 100 mg, about 150 mg, about 200 mg, about 250 mg, about 300 mg, about 350 mg, about 400 mg, about 450 mg, about 500 mg of one or more compounds as disclosed herein in the form of granules for oral suspension. The pharmaceutical compositions further comprise carbomer, castor oil, citric acid, hypromellose phthalate, maltodextrin, potassium sorbate, povidone, silicon dioxide, sucrose, xanthan gum, titanium dioxide and fruit punch flavor.

The pharmaceutical compositions disclosed herein may be disclosed in unit-dosage forms or multiple-dosage forms. Unit-dosage forms, as used herein, refer to physically discrete units suitable for administration to human and animal subjects and packaged individually as is known in the art. Each unit-dose contains a predetermined quantity of the active ingredient(s) sufficient to produce the desired therapeutic effect, in association with the required pharmaceutical carriers or excipients. Examples of unit-dosage forms include ampouls, syringes, and individually packaged tablets and capsules. Unit-dosage forms may be administered in fractions or multiples thereof. A multiple-dosage form is a plurality of identical unit-dosage forms packaged in a single container to be administered in segregated unit-dosage form. Examples of multiple-dosage forms include vials, bottles of tablets or capsules, or bottles of pints or gallons.

The compound as disclosed herein may be administered alone, or in combination with one or more other compounds disclosed herein, one or more other active ingredients. The pharmaceutical compositions that comprise a compound disclosed herein may be formulated in various dosage forms for oral, parenteral, and topical administration. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., Drugs and the Pharmaceutical Science, Marcel Dekker, Inc.: New York, N.Y., 2002; Vol. 126).

The pharmaceutical compositions disclosed herein may be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

In the case wherein the patient's condition does not improve, upon the doctor's discretion the administration of the compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the compounds may be given continuously or temporarily suspended for a certain length of time (i.e., a "drug holiday").

Once improvement of the patient's conditions has occurred, a maintenance dose is administered if necessary. Subsequently, the dosage or the frequency of administration, or both, can be reduced, as a function of the symptoms, to a level at which the improved disease, disorder or condition is retained. Patients can, however, require intermittent treatment on a long-term basis upon any recurrence of symptoms.

A. Oral Administration

The pharmaceutical compositions disclosed herein may be formulated in solid, semisolid, or liquid dosage forms for oral administration. As used herein, oral administration also include buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions disclosed herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions disclosed herein varies upon the type of formulation, and is readily discernible to those of ordinary skill in the art. The pharmaceutical compositions disclosed herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions disclosed herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of nonaqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions disclosed herein may be formulated as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions disclosed herein may be formulated as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms disclosed herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions disclosed herein may be formulated in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) disclosed herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions disclosed herein for oral administration may be also formulated in the forms of liposomes, micelles, microspheres, or nanosystems. Micellar dosage forms can be prepared as described in U.S. Pat. No. 6,350,458.

The pharmaceutical compositions disclosed herein may be formulated as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions disclosed herein may be formulated as immediate or modified release dosage forms, including delayed-, sustained-, pulsed-, controlled, targeted-, and programmed-release forms.

The pharmaceutical compositions disclosed herein may be co-formulated with other active ingredients which do not impair the desired therapeutic action, or with substances that supplement the desired action, such as drotrecogin-, and hydrocortisone.

B. Parenteral Administration

The pharmaceutical compositions disclosed herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions disclosed herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, dimethylacetamide, and dimethylsulfoxide.

Suitable antimicrobial agents or preservatives include, but are not limited to, phenols, cresols, mercurials, benzyl alcohol, chlorobutanol, methyl and propyl p-hydroxybenzates, thimerosal, benzalkonium chloride, benzethonium chloride, methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions disclosed herein may be formulated for single or multiple dosage administration. The single dosage formulations are packaged in an ampule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are formulated as ready-to-use sterile solutions. In another embodiment, the pharmaceutical compositions are formulated as sterile dry soluble products, including lyophilized powders and hypodermic tablets, to be reconstituted with a vehicle prior to use. In yet another embodiment, the pharmaceutical compositions are formulated as ready-to-use sterile suspensions. In yet another embodiment, the pharmaceutical compositions are formulated as sterile dry insoluble products to be reconstituted with a vehicle prior to use. In still another embodiment, the pharmaceutical compositions are formulated as ready-to-use sterile emulsions.

The pharmaceutical compositions disclosed herein may be formulated as immediate or modified release dosage forms, including delayed-, sustained, pulsed-, controlled, targeted-, and programmed-release forms.

The pharmaceutical compositions may be formulated as a suspension, solid, semi-solid, or thixotropic liquid, for administration as an implanted depot. In one embodiment, the pharmaceutical compositions disclosed herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers, such as hydrogels of esters of acrylic and methacrylic acid, collagen, cross-linked polyvinylalcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

D. Modified Release

The pharmaceutical compositions disclosed herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsatile-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions disclosed herein in a modified release dosage form may be fabricated using a matrix controlled release device known to those skilled in the art (see, Takada et al in "Encyclopedia of Controlled Drug Delivery," Vol. 2, Mathiowitz ed., Wiley, 1999).

In one embodiment, the pharmaceutical compositions disclosed herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinylacetate copolymers, ethylene/propylene copolymers, ethylene/ethyl acrylate copolymers, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethyleneterephthalate, natural rubber, silicone rubbers, polydimethylsiloxanes, silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions disclosed herein in a modified release dosage form may be prepared by methods known to those skilled in the art, including direct compression, dry or wet granulation followed by compression, melt-granulation followed by compression.

2. Osmotic Controlled Release Devices

The pharmaceutical compositions disclosed herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s) and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly (acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents are osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as Mannogeme EZ (SPI Pharma, Lewes, DE) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxlated ethylene-vinylacetate, EC, PEG, PPG, PEG/PPG copolymers, PVP, HEC, HPC, CMC, CMEC, HPMC, HPMCP, HPMCAS, HPMCAT, poly (acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions disclosed herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions disclosed herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions disclosed herein in a modified release dosage form may be fabricated a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates may be made by the processes know to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein may be blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

The invention is further illustrated by the following examples:

EXAMPLE 1

5-Methyl-1-phenylpyridin-2(1H)-one

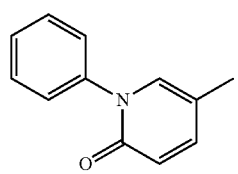

Step 1

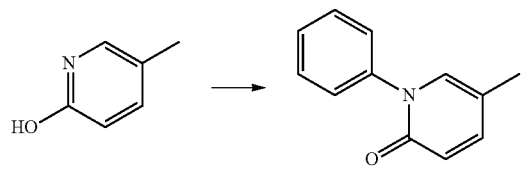

5-Methyl-1-phenyl-1H-pyridin-2-one

A finely pulverized mixture of 2-hydroxy-5-methylpyridine (0.500 g, 4.58 mmol), anhydrous potassium carbonate (0.693 g, 6.41 mmol), copper powder (0.006 g, 0.09 mmol) and iodobenzene (1.68 g, 8.26 mmol) was heated at 180-190° C. for 7 hours. The mixture was cooled, and standard extractive workup was performed to afford a brown residue which was triturated with petroleum ether and recrystallized from hot water to yield the title compound as a white solid (0.470 g, 56%). m.p. 105-107° C.; $^1$H NMR (400 MHz, DMSO-d$_6$) δ 2.50 (s, 3H), 6.43 (d, J=9.3 Hz, 1H), 7.36-7.53 (m, 7H); IR (KBr) υ 3045, 1675, 1611, 1531, 1270 cm$^{-1}$; MS 186 (M+1).

EXAMPLE 2 d$_3$-5-(Methyl-)-1-phenylpyridine-2(1H)-one

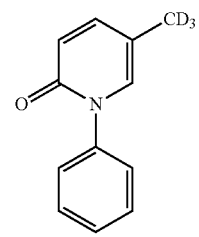 [SMILES: [2H]C([2H])([2H])c1ccc(=O)n(-c2ccccc2)c1]

Step 1

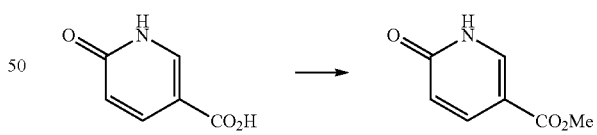

Methyl-6-oxo-1,6-dihydropyridine-3-carboxylate

Thionyl chloride (6.3 mL, 86.33 mmol) was added dropwise to a solution of 6-hydroxynicotinic acid (10.0 g, 71.94 mmol) in methanol at 0° C. The mixture was heated to reflux for 6 hours, the solvent was removed and standard extractive work up provided the title compound as a brown solid (7.5 g, 68%). m.p. 166-172° C.; $^1$H NMR (400 MHz, DMSO-d$_6$) δ 3.77 (s, 3H), 6.37 (d, J=9.3 Hz, 1H), 7.79 (dd, J=2.7, 9.5 Hz, 1H), 8.04 (d, J=2.4 Hz, 1H); IR (KBr) υ 3050, 2965, 1712, 1651, 1433, 1300, 1106 cm$^{-1}$; MS 154 (M+1).

Step 2

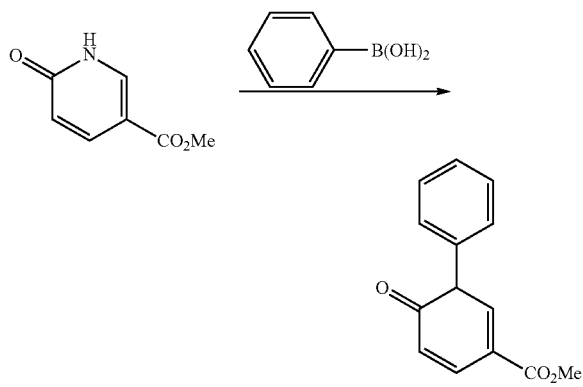

Methyl-6-oxo-1-phenyl-1,6-dihydropyridine-3-carboxylate

Methyl-6-oxo-1,6-dihydropyridine-3-carboxylate (6.0 g, 39.22 mmol), phenylboronic acid (5.74 g, 47.06 mmol), copper(II) acetate monohydrate (11.76 g, 58.82 mmol), pyridine (6.32 mL, 78.43 mmol) and molecular sieves (4 Å, 6.0 g) in dichloromethane (100 mL) was stirred at ambient temperature for 12 hours and filtered. Standard extractive work up provided a crude residue which was purified by silica gel column chromatography (100-200 mesh) (1-2% methanol in chloroform) to give the title compound as a brown solid (5.0 g, 56%). m.p. 100-105° C.; $^1$H NMR (400 MHz, CDCl$_3$) δ 3.86 (s, 3H), 6.63 (d, J=9.5 Hz, 1H), 7.36-7.55 (m, 5H), 7.91 (dd, J=2.5, 9.9 Hz, 1H), 8.23 (d, J=2.5 Hz, 1H); IR (KBr) u 3058, 2924, 2854, 1721, 1675, 1540, 1446, 1313, 1271, 1103 cm$^{-1}$; MS 230 (M+1).

Step 3

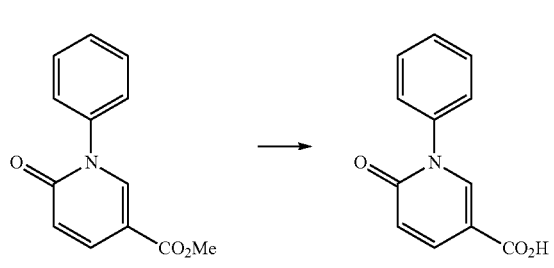 [SMILES: COC(=O)c1ccc(=O)n(-c2ccccc2)c1 ; O=C(O)c1ccc(=O)n(-c2ccccc2)c1]

6-Oxo-1-phenyl-1,6-dihydropyridine-3-carboxylic acid

Lithium hydroxide monohydrate (0.366 g, 8.73 mmol) was added to a mixture of methyl-6-oxo-1-phenyl-1,6-dihydropyridine-3-carboxylate (1.0 g, 4.37 mmol), tetrahydrofuran (9 mL) and water (6 mL) at 0° C. The mixture was stirred for 1 hour, diluted with water and washed with ethyl acetate. The pH of the aqueous layer was adjusted to 2 using 2 N hydrochloric acid and the precipitate was filtered to give the title compound as a brown solid (0.740 g, 79%). m.p. 256-263° C.; $^1$H NMR (400 MHz, DMSO-d$_6$) δ 6.53 (d, J=9.4 Hz, 1H), 7.40-7.49 (m, 5H), 7.87 (dd, J=2.5, 9.8 Hz, 1H), 8.23 (d, J=2.5 Hz, 1H); IR (KBr) u 3446, 1708, 1645, 1577, 1263, 1228 cm$^{-1}$; MS 214 (M−1).

Step 4

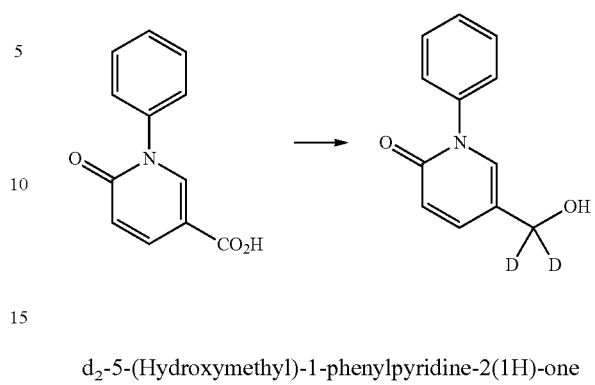

d$_2$-5-(Hydroxymethyl)-1-phenylpyridine-2(1H)-one

Isobutyl chloroformate (0.45 mL, 3.49 mmol) was added to a solution of 6-oxo-1-phenyl-1,6-dihydropyridine-3-carboxylic acid (0.500 g, 2.32 mmol) and N-methylmorpholine (0.38 mL, 3.49 mmol) in tetrahydrofuran (10 mL) at −5° C. The mixture was stirred for 3 hours at the same temperature, diluted with tetrahydrofuran and filtered over a pad of Celite under argon. The filtrate containing the mixed anhydride was added dropwise to a suspension of sodium borodeuteride (0.117 g, 2.79 mmol) in tetrahydrofuran at −10° C. The reaction mixture was allowed to warm to room temperature and stirred for 16 hours, after which D$_2$O (1 mL) was added. Standard extractive work up gave a crude residue which was purified by preparative HPLC to give the title compound as a white solid (0.290 g, 61%). m.p. 115-120° C.; $^1$H NMR (400 MHz, CDCl$_3$) δ 2.05 (br, 1H), 6.66 (d, J=9.1 Hz, 1H), 7.25-7.51 (m, 7H); IR (KBr) u 3337, 1665, 1586, 1535, 1257 cm$^{-1}$; MS 204 (M+1).

Step 5

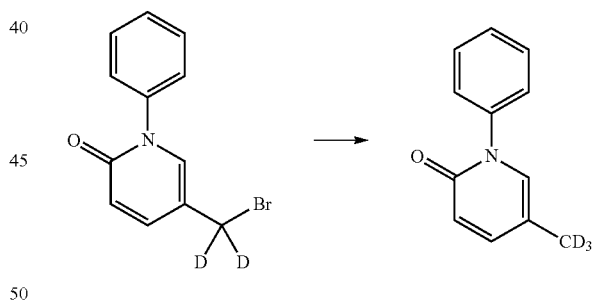

d$_3$-5-(Methyl)-1-phenylpyridine-2(1H)-one

Phosphorus tribromide (0.07 mL, 0.738 mmol) was added dropwise to a solution of d$_2$-5-(hydroxymethyl)-1-phenylpyridine-2(1H)-one (0.300 g, 1.47 mmol) in dichloromethane at −10° C. and the mixture was stirred for 30 minutes. Dichloromethane and excess phosphorus tribromide were flushed out by a stream of argon and the residue was dissolved in tetrahydrofuran. This solution of the bromide was added dropwise to a suspension of lithium aluminum deuteride (0.092 g, 2.2 mmol) in tetrahydrofuran at −78° C. and the mixture was stirred for 1 hour. D$_2$O was added, and standard extractive work up gave a crude residue which was purified by preparative HPLC to give the title compound as a pale brown solid (0.070 g, 25%). m.p. 103-107° C.; $^1$H NMR (400 MHz, DMSO-$d_6$) δ 6.42 (d, J=9.2 Hz, 1H), 7.36-7.53 (m, 7H); IR (KBr) υ 3045, 2925, 1673, 1607, 1488, 1272 cm$^{-1}$; MS 189 (M+1).

EXAMPLE 3

$d_{11}$-5-Methyl-1-phenyl-1H-pyridin-2-one

Step 1

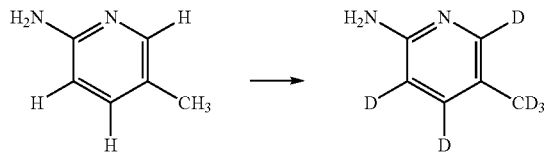

$d_6$-5-methyl-pyridin-2-ylamine

The procedure is carried out using the methods described by by Esaki et al *Tetrahedron* 2006, 62, 10954-10961.

Step 2

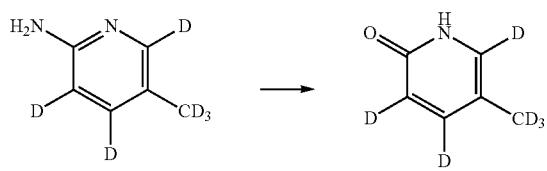 [SMILES: [2H]c1nc(N)c([2H])c([2H])c1C([2H])([2H])[2H] ; [2H]c1[nH]c(=O)c([2H])c([2H])c1C([2H])([2H])[2H]]

$d_6$-5-Methyl-1H-pyridin-2-one

The procedure is carried out using the methods described by Smith et al *Organic Syntheses* 2002, 78, 51-56, but substituting $d_2$-sulfuric acid in deuterium oxide for sulfuric acid in water, and substituting $d_6$-5-methyl-pyridin-2-ylamine for 5-methyl-pyridin-2-ylamine.

Step 3

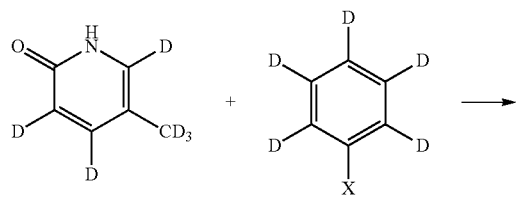

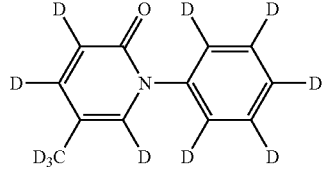

$d_{11}$-5-Methyl-1-phenyl-1H-pyridin-2-one

The procedure is carried out using the methods described in WO2003/014087 wherein the Ullmann coupling is run substituting $d_6$-5-methyl-1H-pyridin-2-one for 5-methyl-1H-pyridin-2-one and also substituting $d_5$-bromobenzene (commercially available from multiple sources) for bromobenzene.

EXAMPLE 4

Human Dose-Escalation Study

The procedure is carried out as described in U.S. Pat. No. 7,635,707, which is hereby incorporated by reference in its entirety.

EXAMPLE 5

Modified Dosing in Response to Liver Function Test Elevations

The procedure is carried out as described in U.S. Pat. No. 7,635,707, which is hereby incorporated by reference in its entirety.

EXAMPLE 6

Multiple-Dose Study

The procedure is carried out as described in US 20070203202, which is hereby incorporated by reference in its entirety.

EXAMPLE 7

Single-Dose Study

The procedure is carried out as described in US 20080287508, which is hereby incorporated by reference in its entirety.

EXAMPLE 8

Multiple-Dose Study

The procedure is carried out as described in US 20080287508, which is hereby incorporated by reference in its entirety.

What is claimed is:

1. A method of administering d-pirfenidone, wherein the d-pirfenidone is administered orally between 30 minutes prior to and 2 hours after consuming food; and wherein at least one position of the d-pirfenidone has deuterium enrichment of no less than about 10%.

2. The method as recited in claim 1, wherein the d-pirfenidone is administered at the same time as consuming food.

3. The method as recited in claim 1, wherein the d-pirfenidone is administered at the same time as a meal.

4. The method as recited in claim 1, wherein the d-pirfenidone is $d_3$-pirfenidone.

5. The method as recited in claim 1, wherein the incidence of adverse events is reduced.

6. The method as recited in claim 5, wherein the adverse event is selected from the group consisting of gastrointestinal upset, nausea, fatigue, somnolence, dizziness, headache, and photosensitivity rash.

7. The method as recited in claim 6, wherein the d-pirfenidone is $d_3$-pirfenidone.

8. The method as recited in claim 1, wherein the patient is advised that the administration of d-pirfenidone with food results in a reduced incidence of adverse events.

9. The method as recited in claim 8, wherein the patient is advised orally.

10. The method as recited in claim 8, wherein the patient is advised in writing.

11. The method as recited in claim 8, wherein the adverse event is selected from the group consisting of nausea, somnolence, and dizziness.

12. The method as recited in claim 8, wherein the d-pirfenidone is $d_3$-pirfenidone.

13. The method as recited in claim 1, wherein the patient is advised that the administration of d-pirfenidone with food reduces the mean maximum plasma concentration of d-pirfenidone in comparison with administering pirfenidone without food.

14. The method as recited in claim 13, wherein the d-pirfenidone is $d_3$-pirfenidone.

15. The method as recited in claim 1, wherein the patient is advised that the administration of d-pirfenidone with food increases the mean absorption half-life of d-pirfenidone in comparison with administering pirfenidone without food.

16. The method as recited in claim 15, wherein the d-pirfenidone is $d_3$-pirfenidone.

17. A kit comprising a pharmaceutical composition of d-pirfenidone, prescribing information, and a container, wherein the prescribing information advises the patient to take the pharmaceutical composition with food.

18. The kit as recited in claim 17, wherein the d-pirfenidone is $d_3$-pirfenidone.

* * * * *